US008119171B2

(12) United States Patent
Lopez et al.

(10) Patent No.: US 8,119,171 B2
(45) Date of Patent: Feb. 21, 2012

(54) METHOD FOR THE PREVENTION OR REDUCTION OF HAZE IN BEVERAGES

(75) Inventors: Michel Lopez, Templeuve (FR); Luppo Edens, JL Rotterdam (NL)

(73) Assignee: DSM IP Assets B.V., Heerlen (NL)

( * ) Notice: Subject to any disclaimer, the term of this patent is extended or adjusted under 35 U.S.C. 154(b) by 2080 days.

(21) Appl. No.: 10/450,022

(22) PCT Filed: Dec. 6, 2001

(86) PCT No.: PCT/NL01/00890
§ 371 (c)(1),
(2), (4) Date: Jun. 6, 2003

(87) PCT Pub. No.: WO02/46381
PCT Pub. Date: Jun. 13, 2002

(65) Prior Publication Data
US 2004/0115306 A1    Jun. 17, 2004

(30) Foreign Application Priority Data

Dec. 7, 2000 (EP) .................................. 00204404
Feb. 26, 2001 (EP) .................................. 01200706
Nov. 15, 2001 (EP) .................................. 01204464

(51) Int. Cl.
C12G 1/00       (2006.01)
C12N 9/48       (2006.01)
C12N 9/60       (2006.01)

(52) U.S. Cl. ........ 426/12; 424/94.63; 530/407; 435/212; 435/219; 435/224

(58) Field of Classification Search .................. None
See application file for complete search history.

(56) References Cited

U.S. PATENT DOCUMENTS

| 3,366,483 | A | | 1/1968 | Stone |
| 3,770,454 | A | * | 11/1973 | Stone .............................. 426/12 |
| 4,181,742 | A | | 1/1980 | Horiuchi et al. |
| 4,532,213 | A | | 7/1985 | Shetty et al. |
| 5,035,902 | A | | 7/1991 | Bilinski et al. |
| 5,192,677 | A | | 3/1993 | Kinsella et al. |
| 6,372,282 | B1 | | 4/2002 | Edens et al. |
| 6,875,456 | B2 | * | 4/2005 | Delest et al. ..................... 426/63 |
| 7,323,327 | B2 | | 1/2008 | Edens et al. |
| 7,608,697 | B2 | | 10/2009 | Edens et al. |
| 2004/0115306 | A1 | | 6/2004 | Lopez et al. |
| 2004/0241664 | A1 | | 12/2004 | Dekker et al. |
| 2004/0241791 | A1 | | 12/2004 | Edens et al. |
| 2005/0064403 | A1 | | 3/2005 | Edens et al. |
| 2006/0257544 | A1 | | 11/2006 | Edens et al. |

FOREIGN PATENT DOCUMENTS

| EP | 0 096 430 A1 | 12/1983 |
| EP | 0 134 048 A1 | 3/1985 |
| EP | 0 184 438 A2 | 6/1986 |
| EP | 0 223 560 | 5/1987 |
| EP | 0 253 455 A1 | 1/1988 |
| EP | 0 301 670 A1 | 2/1989 |
| EP | 321 603 | 6/1989 |
| EP | 325 986 | 8/1989 |
| EP | 0 522 203 | 1/1993 |
| EP | 0522428 | 1/1993 |
| EP | 0 284 603 | 1/1998 |
| EP | 0 967 285 A1 | 12/1999 |
| JP | 53-127896 | 11/1978 |
| JP | 02039896 | 2/1990 |
| JP | 04297923 | 10/1992 |
| JP | 05015314 | 1/1993 |
| JP | 5-344864 | 12/1993 |
| JP | 7-115969 | 5/1995 |
| JP | 09000164 | 1/1997 |
| JP | 9-310645 | 12/1997 |
| JP | 11-221024 | 8/1999 |
| JP | 11-225686 | 8/1999 |
| JP | 11 243866 | 9/1999 |
| WO | WO 86/06097 | 10/1986 |
| WO | WO 96/13174 | 5/1996 |
| WO | 02/45523 A2 | 6/2002 |
| WO | 02/45523 A3 | 6/2002 |
| WO | 02/45524 A2 | 6/2002 |
| WO | 02/46381 A2 | 6/2002 |
| WO | 02/46381 A3 | 6/2002 |
| WO | 02/068623 A2 | 9/2002 |
| WO | 02/045524 A3 | 10/2002 |
| WO | 02/068623 A3 | 12/2002 |

OTHER PUBLICATIONS

Habibi-Najafi et al. Proline-Specific Pepidases of *Lactobacillus casei* Subspecies, J of Dairy Science, vol. 77, No. 2, abstract, 1994.*
Ngo et al. in The Protein Folding Problem and Tertiary Structure Prediction, 1994, Merz et al. (ed.), Birkhauser, Boston, MA, pp. 433 and 492-495.*
Lopez & Edens "Effective prevention of chill-haze in beer using an acid proline-specific endoprotease from *Aspergillus niger*" J. Agric. Food. Chem. 53: 7944-7949 (2005).
Soichi et al, Diazu Tanpakushitsu Eiyo Kenkyukai Kaishi (1985) 6:85-87 (abstract).
Kuwabara et al, "Expression in *Escherichia coli* of the extrinsic 18-kDa protein of photosystem II of spinach" Plant Cell Physiol. 36:435-439 (1995).
Declaration of Luppo Edens executed Oct. 4, 2007 and filed in U.S. Appl. No. 10/433,747.
Arla, "Hydrolysates" 200, printed from internet May 15, 2007.
Godfrey et al. "Beer stabilization" in *Industrial Enzymology*, $2^{nd}$ Ed., Nature Publishing, Chapter 2.6 (Brewing), pp. 124-125 (1996).

(Continued)

*Primary Examiner* — Richard Hutson

(74) *Attorney, Agent, or Firm* — Nixon & Vanderhye P.C.

(57) ABSTRACT

The invention relates to a method for the prevention or reduction of haze in a beverage by the addition of an prolyl-specific endoprotease and to new beverages obtainable by the method according to the invention. It also relates to new endoproteases. Sequence information of a genomic DNA, cDNA as well as protein sequences.

35 Claims, No Drawings

OTHER PUBLICATIONS

Habibi-Najafi et al. "Proline-specific peptidases of *Lactobacillus casei* subspecies" J. Dairy Sci. 77:385-392 (1994).

Nagodawithana et al. (eds.) "Proteases" in *Enzymes in Food Processing*, 3$^{rd}$ Ed., Academic Press, Chapter 16 (Wine), pp. 425-426 (1993).

Nagodawithana et al. (eds.) "Keeping beer clear with chillproofing enzymes" in *Enzymes in Food Processing* 3$^{rd}$ Ed., Academic Press, Chapter 17 (Beer), pp. 448-450 (1993).

Archer et al, "Proteolytic Degradation of Heterologous Proteins Expressed in *Aspergillus Niger*", Biotechnology Letters, vol. 14,No. 5, pp. 357-362, May 1992.

International Search Report for PCTNL/2003/00352, three pages, dated Sep. 29, 2003.

Int'l. Preliminary Examination Report for PCT/NL2003/00352, five pages, dated Oct. 18, 2004.

Altschul et al, "Gapped BLAST and PSI-BLAST: a new generation of protein database search programs", Nucleic Acids Research, 1997, vol. 25, No. 17, 3389-3402.

Brey et al, "The Loss Hydrophobic Polypeptides during Fermentation and Conditioning of High Gravity and Low Gravity Brewed Beer", Journal of the Institute of Brewing, 108(4), 424-433, 2002.

Diefenthal et al, "Rapid purification of proline-specific endopeptidase from *Flavobacterium meningosepticum* heterologously expressed in *Escherichia coil*", World Journal of Microbiology & Biotechnology 11, 209-212 (1995).

Ferreira et al, "The wine proteins", Trends in Food Science & Technolgoy 12 (2002) 230-239.

T. O'Rourke (1996): Brewing. Industrial Enzymology, 2$^{nd}$ Edition, pp. 105-131.

Kanatani et al, "Prolyl Endopeptidase from *Aeromonas hydrophila*: Cloning, Sequencing, and Expression of the Enzyme Gene, and Characterization of the Expressed Enzyme", J. Biochem. 113, 790-796 (1993).

Rapper et al, "*Aspergillus niger* Group", The Genus *Aspergillus*, The Williams & Wilkins Co., Baltimore (1965), pp. 293-344.

Smith et al, "Single-step purification of polypeptides expressed in *Escherichia coli* as fusions with glutathione S-transferase", Gene 67, 31-40 (1988).

Godfrey and West, Industrial Enzymology, 2nd Edition, Chapter 2.6, pp. 124-125, 1996.

Nagodawithana and Reed (eds.), Enzymes in Food Processing, 3rd Edition, Academic Press, Inc., San Diego, Chapter 16, p. 425, 1993.

Nagodawithana and Reed (eds.), Enzymes in Food Processing, 3rd Edition, Academic Press, Inc., San Diego, Chapter V, pp. 448-449, 1993.

Quéméneur et al., Nature (1998) 391:301-304.

Siebert et al., J. Agric. Food Chem. (1996) 44:80-85.

Siebert et al., J. Agric. Food Chem. (1996) 44:1997-2005.

Siebert, J. Agric. Food Chem. (1999) 47:353-362.

Siebert and Lynn, Journal of the American Society of Brewing Chemists (1997) 55(2):73-78.

\* cited by examiner

SEQUENCE LISTING

<160> NUMBER OF SEQ ID NOS: 7

<210> SEQ ID NO 1
<211> LENGTH: 1581
<212> TYPE: DNA
<213> ORGANISM: Aspergillus niger

<400> SEQUENCE: 1

```
atgcgtgcct tctccgctgt cgctgctgcg gccctggcgc tctcttgggc gtctctggct      60
caggctgctc gccccgtct tgtgcccaag cctgtctctc ggccagcctc gagtaaatcg      120
gctgcgacca cgggcgaggc ttactttgag cagctgctgg accatcataa tccggagaag      180 ggcaccttttt cccagaggta ctggtggagt actgaatact ggggtggtcc tgggtcaccg      240
gtcgtcctct ttactcctgg agaggtctct gccgatggct atgaggggta tctcaccaat      300
gggactctca ctggtgtcta tgcgcaggag atccagggtg ccgtcattct cattgagcac      360
cgctactggg gtgattcttc tccttatgag gtgctcaatg ccgaaactct tcagtacctc      420
acactggacc aagccattct ggacatgacc tacttcgccg agacggtgaa gctgcaattc      480
gataacagca cccgcagcaa tgcgcagaat gctccctggg tcatggtcgg tggatcatac      540
agtggtgcct tgacggcttg gaccgaatct gtcgcgcctg aacgttctg ggcttaccat      600 gccactagtg ctcctgtgga ggctatctac gactattggc aatacttttta ccccatccag      660 caaggtatgg cacagaactg cagcaaggac gtgtctctgg tagccgagta tgtcgacaag      720
attggaaaga acggaactgc caaggagcag caggcactca aggaattgtt tggtctggga      780
gctgttgagc attttgatga cttttgccgct gtcctcccca acggaccgta cctctggcaa      840
gacaacgact ttgccacggg atactcttcc ttcttccagt tctgtgacgc cgtcgagggt      900
gtcgaagccg gcgcggcagt aaccccccggc cccgagggtg tcggcctcga aaaggccctg      960
gccaactacg caaactggtt caattcaacc attctccctg attactgcgc aagctacggc      1020
tactggaccg acgaatggag cgtcgcctgc ttcgacagct acaacgcctc gagccccatc      1080
tacaccgata cctccgtagg caatgccgtc gaccgccaat gggaatggtt cctctgcaac      1140
gagcctttct tctactggca ggacggtgct cccgagggta cctccaccat tgtgcccga      1200 ctcgtcagcg cctcctactg gcaacggcaa tgtccgctct acttccccga aacgaacggc      1260
tacacgtacg gcagcgcgaa gggtaagaac gccgccacgt gaacagctg gaccggtgga      1320 tgggatatga cccgcaacac gacgcggttg atctggacga acgggcaata tgacccctgg      1380
cgggactccg gtgtgtcgag cactttccgg cccggtggac cgctggcgag cacggcgaat      1440
gaacccgtgc agattatccc gggcggattc cattgctcgg atttgtatat ggcggattat      1500
```

```
tatgcgaatg aggggggttaa aaaggtggtg gataatgagg tgaagcagat caaggagtgg    1560
gtggaggagt attatgcctg a                                               1581

<210> SEQ ID NO 2
<211> LENGTH: 3290
<212> TYPE: DNA
<213> ORGANISM: Aspergillus niger

<400> SEQUENCE: 2
gagaggcaga aggagtcatt tatcacttgt attccaatgt attttccatt tatagatact      60
gcattcaaat gcaccgttta gcatagcatc ccacattcta tttcattcca atctcatgcc     120
attgccatcc ccggtattaa tttacttctc cgccttatct tgcaatcttg caatctcttt     180
ctcctcgtta tcacgcgttc ctgcaggcgc acctccgatg gcactgcagc cggagtcccc     240
gcggcgccgg cactactaaa gactaaagtg tctagtctag cctccaatgt gctcacctcc     300
atcagcatct catccattta tcttctgacg atgtcatctg caggctccac cccctccggc     360
cgccccgacg ctctccgacg gtgcacaaca atcaattctg cagtcacgct caagattcgt     420
ccctgccgga ctcctcatgc cgtgcctggt ttaatctatg caatggagta aggtagtatc     480
gcctagcagg agcggagttc ctgctgcgct cacgccatgg tgccggcgca gacataaatc     540
gctcgtttcc tccggcgctg gccgttctct cgagccagtt tgtctgttgt ggttgtagga     600
tcctctgttc ccctcgacag ctcacaatgc gttccttctc cgttgtcgct gccgcgtcac     660
tggcgctctc ttgggcgtct ctggcccagg ctgctcgccc ccgtcttgtg cccaagccta     720
tctctcggcc agcttcgagt aagtcggctg cgactacggg tgaggcttat tttgagcagc     780
tgctggacca tcacaacccg gagaagggaa cgttttccca gcggtactgg tggagtactg     840
aatactgggg tggacctggg tcaccggtgc gtctctgaca tttggtctta tgaccggcca     900
tattgaaact tagccggtgg caaggtccgc aatcatgagg aacattgctg attaaactag     960
gtggtcctct ttaaccctgg agaggtctct gccgatggct atgagggggta tctccaccaac    1020 gatactctca ctggtgtcta tgcgcaggag atccagggtg ccgtcattct cattgaacgt    1080
gagtgtcact gctaccatgg aaaaaagaca ttcgctgatc gaccccaatc tagaccgcta    1140
ctggggcgac tcttcgcctt atgaggtgct caatgccgaa acacttcagt atctcacact    1200
ggatcagtcc attctggaca tgacctactt cgccgagacg gtaaagctgc agttcgataa    1260
tagcagccgc agcaatgcgc agaatgctgt atgttacctt caccgctcta tgtttctgat    1320
aggtactgac aacgtagccc tgggtcatgg tcggtggctc atacagcggt gccttgacgg    1380
cttggaccga gtctatcgcg cctggaacgt tctgggctta ccatgccacc agtgcgcctg    1440
tggaggctat ctatgacttt gtaggtgtag cctgctcttg ttatctatac ttgcagctaa    1500
ccaagccagt ggcaatactt ctaccccatt cagcaaggta tggcacagaa ctgcagcaag    1560
gatgtgtctc tggtagccga gtatgtcgac aaaattggga agaatggaac tgccaaggaa    1620
cagcaggagc tcaaagaatt gtttggtctg ggagctgttg agcattacga tgactttgcc    1680
gcgtgagtac ttcaaagtct atagacgagc ttttctgaca ggaacagtgt cctgcccaac    1740
ggaccgtacc tctggcaaga caacgacttt gtcacaggat actcttcctt cttccagttc    1800
tgtgatgctg tcgaggtgag ttaccaccag attcctcttg attgaagcaa tatactaacg    1860
gacacagggt gtcgaagccg gcgcggcagt gaccccggc cccgagggcg tcggacttga    1920
aaaggccctg ccaactacg caaactggtt caattcaacc atactcccta actgtatttc    1980
accatctctt gtctcgttcc tctcccttat cctcccagac taacctagtg acagactgcg    2040
```

-continued

| | |
|---|---|
| caagctacgg ctactggacc gacgaatgga gcgtcgcctg tttcgacagc tataatgcct | 2100 |
| cgagccccat cttcaccgac acctccgtgg gtaaccctgt cgaccgccaa tgggaatggt | 2160 |
| tcctctgcaa cgagccttt ttctggtggc aggagtgcgt accccttacc tcattcatga | 2220 |
| taacacacga acaattccac taacaaagat ccagcggtgc ccccgaggga acctccacta | 2280 |
| ttgtgccccg gctcgtcagc gcctcctact ggcaacgcca atgcccgctc tacttccccg | 2340 |
| aagttaacgg ctacacgtac ggcagcgcga agggtaaaaa ctccgctacg gtgaacagct | 2400 |
| ggacgggtgg atgggatatg acccgcaaca cgacgcggtt gatctggacg aacgggtagg | 2460 |
| tctccccta atttccgttg aatgtgatgt gaagataaac tcaatgctaa taaattgaga | 2520 |
| aggcaatatg accctggcg cgactccggt gtgtcgagca ctttccggcc cggtggtccg | 2580 |
| ctggttagca cggcgaacga acccgtgcag attattccgg gcgggttcca ttgctcggac | 2640 |
| ttgtatatgg aggattacta tgcgaatgag ggtgtgagga aggtggttga taatgaggtg | 2700 |
| aagcagatta aggagtgggt ggaggagtat tatgcttgat gaagatactg gtggacatat | 2760 |
| ggagtgtaca taagatgaat ggtcataaaa tgatgatggt agatacggct atggctgttg | 2820 |
| attagatggt cctttcgcat ttcctaatta ctgagcacgt gctccatggt atgggaagtg | 2880 |
| gagacgttgc tatatatatt gactgtcggg ctattgttca cggcgtagaa gctagacgct | 2940 |
| ttgtctatgt ggccttcact aaagaccgtg actctgccca gtcttccccc cttcgaggac | 3000 |
| ctggtattag ccaaacccac ccacaaacct aacaaagatc atcgtgacat tgaagtcact | 3060 |
| ctaggtactg ctggcgctga ttacagtggc tcaattcgaa catttcaaca gcacataagg | 3120 |
| gaagggtcgc ttcacttgct accttgatac gaaagcagcc acgcccaaca cttataggg | 3180 |
| tgacaaccat cggcatgctg ggttatctac tatatctcct gattctgtgg atcctggaga | 3240 |
| tcgatctggt acactaatct actacaatgc atgtgaagta gggataggca | 3290 |

<210> SEQ ID NO 3
<211> LENGTH: 1581
<212> TYPE: DNA
<213> ORGANISM: Aspergillus niger

<400> SEQUENCE: 3

| | |
|---|---|
| atgcgttcct tctccgttgt cgctgccgcg tcactggcgc tctcttgggc gtctctggcc | 60 |
| caggctgctc gccccgtct tgtgcccaag cctatctctc ggccagcttc gagtaagtcg | 120 |
| gctgcgacta cgggtgaggc ttatttgag cagctgctgg accatcacaa cccggagaag | 180 |
| ggaacgtttt cccagcggta ctggtggagt actgaatact ggggtggacc tgggtcaccg | 240 |
| gtggtcctct ttaaccctgg agaggtctct gccgatggct atgaggggta tctcaccaac | 300 |
| gatactctca ctggtgtcta tgcgcaggag atccagggtg ccgtcattct cattgaacac | 360 |
| cgctactggg gcgactcttc gccttatgag gtgctcaatg ccgaaacact tcagtatctc | 420 |
| acactggatc agtccattct ggacatgacc tacttcgccg agacggtaaa gctgcagttc | 480 |
| gataatagca gccgcagcaa tgcgcagaat gctccctggg tcatggtcgg tggctcatac | 540 |
| agcggtgcct tgacggcttg gaccgagtct atcgcgcctg gaacgttctg ggcttaccat | 600 |
| gccaccagtg cgcctgtgga ggctatctat gactttggc aatacttcta ccccattcag | 660 |
| caaggtatgg cacagaactg cagcaaggat gtgtctctgg tagccgagta tgtcgacaaa | 720 |
| attgggaaga atggaactgc caaggaacag caggagctca agaattgtt tggtctggga | 780 |
| gctgttgagc attacgatga cttttgccgct gtcctgccca cggaccgta cctctggcaa | 840 |
| gacaacgact ttgtcacagg atactcttcc ttcttccagt tctgtgatgc tgtcgagggt | 900 |

-continued

```
gtcgaagccg gcgcggcagt gaccccggc cccgagggcg tcggacttga aaaggccctg    960
gccaactacg caaactggtt caattcaacc atactcccta actactgcgc aagctacggc   1020
tactggaccg acgaatggag cgtcgcctgt ttcgacagct ataatgcctc gagccccatc   1080
ttcaccgaca cctccgtggg taaccctgtc gaccgccaat gggaatggtt cctctgcaac   1140
gagcctttct tctggtggca ggacggtgcc cccgagggaa cctccactat tgtgccccgg   1200
ctcgtcagcg cctcctactg gcaacgccaa tgcccgctct acttcccga agttaacggc    1260 tacacgtacg gcagcgcgaa gggtaaaaac tccgctacgg tgaacagctg acgggtgga    1320 tgggatatga cccgcaacac gacgcggttg atctggacga acgggcaata tgaccccctgg  1380 cgcgactccg gtgtgtcgag cactttccgg cccggtggtc cgctggttag cacggcgaac   1440
gaacccgtgc agattattcc gggcgggttc cattgctcgg acttgtatat ggaggattac   1500
tatgcgaatg agggtgtgag gaaggtggtt gataatgagg tgaagcagat taaggagtgg   1560
gtggaggagt attatgcttg a                                             1581
```

<210> SEQ ID NO 4
<211> LENGTH: 526
<212> TYPE: PRT
<213> ORGANISM: Aspergillus niger

<400> SEQUENCE: 4

```
Met Arg Ser Phe Ser Val Val Ala Ala Ala Ser Leu Ala Leu Ser Trp
  1               5                  10                  15

Ala Ser Leu Ala Gln Ala Ala Arg Pro Arg Leu Val Pro Lys Pro Ile
             20                  25                  30

Ser Arg Pro Ala Ser Ser Lys Ser Ala Ala Thr Thr Gly Glu Ala Tyr
         35                  40                  45

Phe Glu Gln Leu Leu Asp His His Asn Pro Glu Lys Gly Thr Phe Ser
     50                  55                  60

Gln Arg Tyr Trp Trp Ser Thr Glu Tyr Trp Gly Gly Pro Gly Ser Pro
 65                  70                  75                  80

Val Val Leu Phe Asn Pro Gly Glu Val Ser Ala Asp Gly Tyr Glu Gly
                 85                  90                  95

Tyr Leu Thr Asn Asp Thr Leu Thr Gly Val Tyr Ala Gln Glu Ile Gln
            100                 105                 110

Gly Ala Val Ile Leu Ile Glu His Arg Tyr Trp Gly Asp Ser Ser Pro
        115                 120                 125

Tyr Glu Val Leu Asn Ala Glu Thr Leu Gln Tyr Leu Thr Leu Asp Gln
    130                 135                 140

Ser Ile Leu Asp Met Thr Tyr Phe Ala Glu Thr Val Lys Leu Gln Phe
145                 150                 155                 160

Asp Asn Ser Ser Arg Ser Asn Ala Gln Asn Ala Pro Trp Val Met Val
                165                 170                 175

Gly Gly Ser Tyr Ser Gly Ala Leu Thr Ala Trp Thr Glu Ser Ile Ala
            180                 185                 190

Pro Gly Thr Phe Trp Ala Tyr His Ala Thr Ser Ala Pro Val Glu Ala
        195                 200                 205

Ile Tyr Asp Phe Trp Gln Tyr Phe Tyr Pro Ile Gln Gln Gly Met Ala
    210                 215                 220

Gln Asn Cys Ser Lys Asp Val Ser Leu Val Ala Glu Tyr Val Asp Lys
225                 230                 235                 240

Ile Gly Lys Asn Gly Thr Ala Lys Glu Gln Gln Glu Leu Lys Glu Leu
                245                 250                 255
```

```
Phe Gly Leu Gly Ala Val Glu His Tyr Asp Asp Phe Ala Ala Val Leu
            260                 265                 270

Pro Asn Gly Pro Tyr Leu Trp Gln Asp Asn Asp Phe Val Thr Gly Tyr
        275                 280                 285

Ser Ser Phe Phe Gln Phe Cys Asp Ala Val Glu Gly Val Glu Ala Gly
    290                 295                 300

Ala Ala Val Thr Pro Gly Pro Glu Gly Val Gly Leu Glu Lys Ala Leu
305                 310                 315                 320

Ala Asn Tyr Ala Asn Trp Phe Asn Ser Thr Ile Leu Pro Asn Tyr Cys
                325                 330                 335

Ala Ser Tyr Gly Tyr Trp Thr Asp Glu Trp Ser Val Ala Cys Phe Asp
            340                 345                 350

Ser Tyr Asn Ala Ser Ser Pro Ile Phe Thr Asp Thr Ser Val Gly Asn
        355                 360                 365

Pro Val Asp Arg Gln Trp Glu Trp Phe Leu Cys Asn Glu Pro Phe Phe
    370                 375                 380

Trp Trp Gln Asp Gly Ala Pro Glu Gly Thr Ser Thr Ile Val Pro Arg
385                 390                 395                 400

Leu Val Ser Ala Ser Tyr Trp Gln Arg Gln Cys Pro Leu Tyr Phe Pro
                405                 410                 415

Glu Val Asn Gly Tyr Thr Tyr Gly Ser Ala Lys Gly Lys Asn Ser Ala
            420                 425                 430

Thr Val Asn Ser Trp Thr Gly Gly Trp Asp Met Thr Arg Asn Thr Thr
        435                 440                 445

Arg Leu Ile Trp Thr Asn Gly Gln Tyr Asp Pro Trp Arg Asp Ser Gly
    450                 455                 460

Val Ser Ser Thr Phe Arg Pro Gly Gly Pro Leu Val Ser Thr Ala Asn
465                 470                 475                 480

Glu Pro Val Gln Ile Ile Pro Gly Gly Phe His Cys Ser Asp Leu Tyr
                485                 490                 495

Met Glu Asp Tyr Tyr Ala Asn Glu Gly Val Arg Lys Val Val Asp Asn
            500                 505                 510

Glu Val Lys Gln Ile Lys Glu Trp Val Glu Glu Tyr Tyr Ala
        515                 520                 525

<210> SEQ ID NO 5
<211> LENGTH: 526
<212> TYPE: PRT
<213> ORGANISM: Aspergillus niger

<400> SEQUENCE: 5

Met Arg Ala Phe Ser Ala Val Ala Ala Ala Leu Ala Leu Ser Trp
1               5                   10                  15

Ala Ser Leu Ala Gln Ala Ala Arg Pro Arg Leu Val Pro Lys Pro Val
                20                  25                  30

Ser Arg Pro Ala Ser Ser Lys Ser Ala Ala Thr Thr Gly Glu Ala Tyr
            35                  40                  45

Phe Glu Gln Leu Leu Asp His His Asn Pro Glu Lys Gly Thr Phe Ser
        50                  55                  60

Gln Arg Tyr Trp Trp Ser Thr Glu Tyr Trp Gly Gly Pro Gly Ser Pro
65                  70                  75                  80

Val Val Leu Phe Thr Pro Gly Glu Val Ser Ala Asp Gly Tyr Glu Gly
                85                  90                  95

Tyr Leu Thr Asn Gly Thr Leu Thr Gly Val Tyr Ala Gln Glu Ile Gln
            100                 105                 110
```

```
Gly Ala Val Ile Leu Ile Glu His Arg Tyr Trp Gly Asp Ser Ser Pro
            115                 120                 125

Tyr Glu Val Leu Asn Ala Glu Thr Leu Gln Tyr Leu Thr Leu Asp Gln
130                 135                 140

Ala Ile Leu Asp Met Thr Tyr Phe Ala Glu Thr Val Lys Leu Gln Phe
145                 150                 155                 160

Asp Asn Ser Thr Arg Ser Asn Ala Gln Asn Ala Pro Trp Val Met Val
            165                 170                 175

Gly Gly Ser Tyr Ser Gly Ala Leu Thr Ala Trp Thr Glu Ser Val Ala
            180                 185                 190

Pro Gly Thr Phe Trp Ala Tyr His Ala Thr Ser Ala Pro Val Glu Ala
            195                 200                 205

Ile Tyr Asp Tyr Trp Gln Tyr Phe Tyr Pro Ile Gln Gln Gly Met Ala
210                 215                 220

Gln Asn Cys Ser Lys Asp Val Ser Leu Val Ala Glu Tyr Val Asp Lys
225                 230                 235                 240

Ile Gly Lys Asn Gly Thr Ala Lys Glu Gln Gln Ala Leu Lys Glu Leu
            245                 250                 255

Phe Gly Leu Gly Ala Val Glu His Phe Asp Asp Phe Ala Ala Val Leu
            260                 265                 270

Pro Asn Gly Pro Tyr Leu Trp Gln Asp Asn Asp Phe Ala Thr Gly Tyr
            275                 280                 285

Ser Ser Phe Phe Gln Phe Cys Asp Ala Val Glu Gly Val Glu Ala Gly
            290                 295                 300

Ala Ala Val Thr Pro Gly Pro Glu Gly Val Gly Leu Glu Lys Ala Leu
305                 310                 315                 320

Ala Asn Tyr Ala Asn Trp Phe Asn Ser Thr Ile Leu Pro Asp Tyr Cys
            325                 330                 335

Ala Ser Tyr Gly Tyr Trp Thr Asp Glu Trp Ser Val Ala Cys Phe Asp
            340                 345                 350

Ser Tyr Asn Ala Ser Ser Pro Ile Tyr Thr Asp Thr Ser Val Gly Asn
            355                 360                 365

Ala Val Asp Arg Gln Trp Glu Trp Phe Leu Cys Asn Glu Pro Phe Phe
370                 375                 380

Tyr Trp Gln Asp Gly Ala Pro Glu Gly Thr Ser Thr Ile Val Pro Arg
385                 390                 395                 400

Leu Val Ser Ala Ser Tyr Trp Gln Arg Gln Cys Pro Leu Tyr Phe Pro
            405                 410                 415

Glu Thr Asn Gly Tyr Thr Tyr Gly Ser Ala Lys Gly Lys Asn Ala Ala
            420                 425                 430

Thr Val Asn Ser Trp Thr Gly Gly Trp Asp Met Thr Arg Asn Thr Thr
            435                 440                 445

Arg Leu Ile Trp Thr Asn Gly Gln Tyr Asp Pro Trp Arg Asp Ser Gly
450                 455                 460

Val Ser Ser Thr Phe Arg Pro Gly Gly Pro Leu Ala Ser Thr Ala Asn
465                 470                 475                 480

Glu Pro Val Gln Ile Ile Pro Gly Gly Phe His Cys Ser Asp Leu Tyr
            485                 490                 495

Met Ala Asp Tyr Tyr Ala Asn Glu Gly Val Lys Lys Val Val Asp Asn
            500                 505                 510

Glu Val Lys Gln Ile Lys Glu Trp Val Glu Glu Tyr Tyr Ala
            515                 520                 525

<210> SEQ ID NO 6
```

<211> LENGTH: 1551
<212> TYPE: DNA
<213> ORGANISM: Aspergillus niger

<400> SEQUENCE: 6

```
atgcgttcct tctccgttgt cgctgccgcg tcactggcgc tctcttgggc gtctctggcc      60
caggctgctc gccccgtct tgtgcccaag cctatctctc ggccagcttc gagtaagtcg      120
gctgcgacta cgggtgaggc ttattttgag cagctgctgg accatcacaa cccggagaag      180
ggaacgtttt cccagcggta ctggtggagt actgaatact ggggtggacc tgggtcaccg      240
gtggtcctct ttaaccctgg agaggtctct gccgatggc atgaggggta tctcaccaac       300
gatactctca ctggtgtcta tgcgcaggag atccagggtg ccgtcattct cattgaacac      360
cgctactggg gcgactcttc gccttatgag gtgctcaatg ccgaaacact tcagtatctc      420
acactggatc agtccattct ggacatgacc tacttcgccg agacggtaaa gctgcagttc      480
gataatagca gccgcagcaa tgcgcagaat gctccctggg tcatggtcgg tggctcatac      540
agcggtgcct tgacggcttg gaccgagtct atcgcgcctg aacgttctg gcttaccat       600
gccaccagtg cgcctgtgga ggctatctat gactttcaag gtatggcaca gaactgcagc      660
aaggatgtgt ctctggtagc cgagtatgtc gacaaaattg gaagaatgg aactgccaag      720
gaacagcagg agctcaaaga attgtttggt ctgggagctg ttgagcatta cgatgacttt      780
gccgctgtcc tgcccaacgg accgtacctc tggcaagaca cgactttgt cacaggatac      840
tcttccttct tccagttctg tgatgctgtc gagggtgtcg aagccggcgc ggcagtgacc      900
cccggccccg agggcgtcgg acttgaaaag gccctggcca actacgcaaa ctggttcaat      960
tcaaccatac tccctaacta ctgcgcaagc tacggctact ggaccgacga atggagcgtc      1020
gcctgtttcg acagctataa tgcctcgagc cccatcttca ccgacacctc cgtgggtaac      1080
cctgtcgacc gccaatggga atggttcctc tgcaacgagc ctttcttctg gtggcaggac      1140
ggtgccccg agggaacctc cactattgtg ccccggctcg tcagcgcctc ctactggcaa      1200
cgccaatgcc cgctctactt ccccgaagtt aacggctaca cgtacggcag cgcgaagggt      1260
aaaaactccg ctacggtgaa cagctggacg ggtggatggg atatgacccg caacacgacg      1320
cggttgatct ggacgaacgg gcaatatgac ccctggcgcg actccggtgt gtcgagcact      1380
ttccggcccg gtggtccgct ggttagcacg gcgaacgaac ccgtgcagat tattccgggc      1440
gggttccatt gctcggactt gtatatggag gattactatg cgaatgaggg tgtgaggaag      1500
gtggttgata tgaggtgaa gcagattaag gaatacggct atggctgttg a               1551
```

<210> SEQ ID NO 7
<211> LENGTH: 516
<212> TYPE: PRT
<213> ORGANISM: Aspergillus niger

<400> SEQUENCE: 7

```
Met Arg Ser Phe Ser Val Val Ala Ala Ala Ser Leu Ala Leu Ser Trp
  1               5                  10                  15

Ala Ser Leu Ala Gln Ala Ala Arg Pro Arg Leu Val Pro Lys Pro Ile
             20                  25                  30

Ser Arg Pro Ala Ser Ser Lys Ser Ala Ala Thr Thr Gly Glu Ala Tyr
         35                  40                  45

Phe Glu Gln Leu Leu Asp His His Asn Pro Glu Lys Gly Thr Phe Ser
     50                  55                  60

Gln Arg Tyr Trp Trp Ser Thr Glu Tyr Trp Gly Gly Pro Gly Ser Pro
 65                  70                  75                  80
```

-continued

Val Val Leu Phe Asn Pro Gly Glu Val Ser Ala Asp Gly Tyr Glu Gly
                85                  90                  95

Tyr Leu Thr Asn Asp Thr Leu Thr Gly Val Tyr Ala Gln Glu Ile Gln
               100                 105                 110

Gly Ala Val Ile Leu Ile Glu His Arg Tyr Trp Gly Asp Ser Ser Pro
               115                 120                 125

Tyr Glu Val Leu Asn Ala Glu Thr Leu Gln Tyr Leu Thr Leu Asp Gln
           130                 135                 140

Ser Ile Leu Asp Met Thr Tyr Phe Ala Glu Thr Val Lys Leu Gln Phe
145                 150                 155                 160

Asp Asn Ser Ser Arg Ser Asn Ala Gln Asn Ala Pro Trp Val Met Val
               165                 170                 175

Gly Gly Ser Tyr Ser Gly Ala Leu Thr Ala Trp Thr Glu Ser Ile Ala
               180                 185                 190

Pro Gly Thr Phe Trp Ala Tyr His Ala Thr Ser Ala Pro Val Glu Ala
           195                 200                 205

Ile Tyr Asp Phe Gln Gly Met Ala Gln Asn Cys Ser Lys Asp Val Ser
           210                 215                 220

Leu Val Ala Glu Tyr Val Asp Lys Ile Gly Lys Asn Gly Thr Ala Lys
225                 230                 235                 240

Glu Gln Gln Glu Leu Lys Glu Leu Phe Gly Leu Gly Ala Val Glu His
               245                 250                 255

Tyr Asp Asp Phe Ala Ala Val Leu Pro Asn Gly Pro Tyr Leu Trp Gln
               260                 265                 270

Asp Asn Asp Phe Val Thr Gly Tyr Ser Ser Phe Phe Gln Phe Cys Asp
           275                 280                 285

Ala Val Glu Gly Val Glu Ala Gly Ala Val Thr Pro Gly Pro Glu
           290                 295                 300

Gly Val Gly Leu Glu Lys Ala Leu Ala Asn Tyr Ala Asn Trp Phe Asn
305                 310                 315                 320

Ser Thr Ile Leu Pro Asn Tyr Cys Ala Ser Tyr Gly Tyr Trp Thr Asp
               325                 330                 335

Glu Trp Ser Val Ala Cys Phe Asp Ser Tyr Asn Ala Ser Ser Pro Ile
               340                 345                 350

Phe Thr Asp Thr Ser Val Gly Asn Pro Val Asp Arg Gln Trp Glu Trp
           355                 360                 365

Phe Leu Cys Asn Glu Pro Phe Phe Trp Trp Gln Asp Gly Ala Pro Glu
370                 375                 380

Gly Thr Ser Thr Ile Val Pro Arg Leu Val Ser Ala Ser Tyr Trp Gln
385                 390                 395                 400

Arg Gln Cys Pro Leu Tyr Phe Pro Glu Val Asn Gly Tyr Thr Tyr Gly
               405                 410                 415

Ser Ala Lys Gly Lys Asn Ser Ala Thr Val Asn Ser Trp Thr Gly Gly
               420                 425                 430

Trp Asp Met Thr Arg Asn Thr Thr Arg Leu Ile Trp Thr Asn Gly Gln
           435                 440                 445

Tyr Asp Pro Trp Arg Asp Ser Gly Val Ser Ser Thr Phe Arg Pro Gly
           450                 455                 460

Gly Pro Leu Val Ser Thr Ala Asn Glu Pro Val Gln Ile Ile Pro Gly
465                 470                 475                 480

Gly Phe His Cys Ser Asp Leu Tyr Met Glu Asp Tyr Tyr Ala Asn Glu
               485                 490                 495

```
Gly Val Arg Lys Val Val Asp Asn Glu Val Lys Gln Ile Lys Glu Tyr
            500                 505                 510
Gly Tyr Gly Cys
        515
```

METHOD FOR THE PREVENTION OR REDUCTION OF HAZE IN BEVERAGES

CROSS-REFERENCE TO RELATED APPLICATION

This application is the national phase of PCT application PCT/NL01/00890 having an international filing date of 6 Dec. 2001, which claims priority from European applications EP 01204464.0 filed 15 Nov. 2001; EP 01200706.8 filed 26 Feb. 2001; and EP 00204404.8 filed 7 Dec. 2000. The contents of these documents are incorporated herein by reference.

The invention relates to a method for the prevention or reduction of haze in a beverage by the addition of an endoprotease and to new beverages obtainable by the method according to the invention. It also relates to new endoproteases.

Haze is a well known phenomenon in the beverage industry. Haze can for example be present in beer, wine and fruit juice. Haze formation can occur at different stages during the brewing process. In "Enzymes in food processing" edited by T. Nagodawithana and G. Reed, $3^{rd}$ edition, Academic press Inc., San Diego, Chapter V, p. 448-449, it has been proposed that the haze in beer is the result of interactions between beer proteins and polyphenolic procyanidins. It is explained that in beer haze is often formed upon chilling of the beer. Beer is fermented and then maturated, often under chilled conditions. To achieve clarity, beer is often filtered while cold. In spite of the filtration, beer often becomes cloudy after it is packaged and distributed to customers and chilled again before serving. Eventually haze is even formed in beer when it is not or no longer chilled and a sediment may develop. Haze formation is undesirable because the cloudiness caused by haze formation resembles cloudiness produced by microbial spoilage, which is undesirable, especially for bright beers.

In "Industrial Enzymology", $2^{nd}$ edition, Chapter 2.6, p. 124-125, it has been described that haze in beer can result form the cross-linkage of the high molecular weight hordein fraction of malt, containing a high proportion of hydrophobic amino acids, which combines with polyphenols principally consisting of proanthocyanidins and catechins (flavanoids). It is described that small amounts of carbohydrates and trace mineral ions are also involved in haze formation, as well as oxidation, which is stated to play an important part in polymerization of polyphenols to produce irreversible haze. It is proposed that polyphenols combine slowly with protein to form chill haze when cooled, but which redissolve when warmed up. Eventually, however, as polyphenols polymerize and increase in size they become insoluble at room temperature to form irreversible or permanent haze.

In several other publications it has been proposed that the formation of haze in for example beer, wine and fruit juice, coffees and teas is the result of interactions between proteins and polyphenols (K. J. Siebert et al, J. Agric. Food Chem. 44 (1996) 1997-2005 and K. J. Siebert et al, J. Agric. Food Chem. 44 (1996) 80-85, K. J. Siebert, J. Agric. Food Chem. 47 (1999) 353-362).

Since its discovery by L. Wallerstein in 1911, it has been known that a method for the reduction of chill haze formation in beer is the addition of papain to the beer. Papain is an extract of papaya having proteolytic activity. In "Enzymes in food processing" edited by T. Nagodawithana and G. Reed, $3^{rd}$ edition, Academic press Inc., San Diego, Chapter V, p. 448-449 papain is described as being far superior to any other enzyme for the prevention of chill haze in beer. The exact mechanism by which papain works, however, has never been determined ("Enzymes in food processing" edited by T. Nagodawithana and G. Reed, $3^{rd}$ edition, Academic press Inc., San Diego, Chapter V, p. 448-449).

A disadvantage of the use of papain however, is that it has a negative effect on foam. Proteins are necessary to form stable foam on beer. By its proteolytic activity, however, papain adversely affects head foam stability.

Haze formation in wine has been discussed in e.g. "Enzymes in food processing" edited by T. Nagodawithana and G. Reed, $3^{rd}$ edition, Academic press Inc., San Diego, Chapter 16, p. 425, where it is described that grape proteins are held responsible for the formation of haze during the storage of wine. If precipitation is formed in wine after bottling, the wine becomes less attractive to the consumer, which will affect sales. To prevent precipitation, for example bentonite is used. Although bentonite and other adsorbents are successful in removing the proteins, it is not selective and removes other desirable compounds from wine, often affecting the organoleptic properties of wine. In addition, the use of bentonite results in a considerable loss of wine and it the dumping of waste containing bentonite presents difficulties.

Although the mechanism is not well understood, it is assumed that the addition of papain hydrolyses the protein in beer to such an extent that a protein-polyphenol haze is not formed or is formed to a smaller extent. Bentonite is used for a similar reason in wine: by absorbing proteins it prevents the formation of protein-polyphenol haze and precipitates. Instead of removing the protein, however, polyphenols may be removed to reduce or prevent haze formation. A typical example of a compound used to remove polyphenols from beverages is polyvinylpolypyrrolidon (PVPP). Lately it has been recognized that polyphenols are important anti-oxidants. Because of all the beneficial effects attributed to antioxidants, the option of removing polyphenols from beverages is not the most attractive way to prevent the formation of haze.

Since all known techniques for the prevention or removal of haze have drawbacks, there is still a need for a new method for the prevention or reduction of haze in beverages.

It is an object of the present invention to provide a method for the prevention or reduction of haze in a beverage.

Surprisingly, it has been found that this object is achieved by providing a method for the prevention or reduction of haze in a beverage wherein a prolyl-specific endoprotease is added to the beverage.

In the framework of this invention the term "beverage" includes beverages in all stages of their preparation. Thus, a beverage is not only a beverage ready for consumption but also any composition used to prepare the beverage. For example, wort as used in beer preparation is encompassed by the term "beverage" as used herein. Also, the addition of a prolyl-specific endoprotease during the preparation of a beverage to compositions that are not or not entirely liquid is intended to fall within the method according to the invention. A prolyl-specific endoprotease added to a mash at the start of beer brewing is an example of such a composition.

A prolyl specific endoprotease is defined as an endoprotease that cuts proteins or peptides near or at places where the protein or peptide contains a prolyl-residue in its chain. Preferably, a prolyl specific endoprotease is an endoprotease that cuts proteins or peptides at places where the protein or peptide contains a prolyl-residue. In the method according to the invention, a prolyl-specific endoprotease is preferably used that cuts prolyl-residues at their C-terminus. A prolyl-specific endoprotease that cuts prolyl-residues at their NH2-terminus is for example described in a publication in Nature of 15 Jan. 1998, Vol. 391, pp. 301-304.

In this text, the terms prolyl-specific endoprotease, proline-specific endoprotease, proline-specific endopeptidase and peptide having a prolyl-specific activity or similar expressions are used interchangeably.

In this text, the words peptide and protein are used interchangeably. In this text, the words "haze", "cloudiness" and "turbidity" are also used interchangeably. To quantify the amount of haze in a beverage, a turbidimeter is often used. In a turbiditimeter the amount of light is measured that is scattered at a prediscribed angle relative to the direction of the incident light beam. Turbidity measurements are very suitable for the measurement of haze formed as the result of protein-polyphenol interactions.

A polyphenol is defined as a compound having a chemical structure which structure contains at least two aromatic rings substituted with at least one hydroxyl group or having a chemical structure which contains at least one aromatic ring substituted with at least two hydroxyl groups.

Examples of polyphenols are tannins and flavonoids, which include for example catechins, flavanols and anthocyanins.

Endoproteases having a prolyl-specific activity are known (E.C. 3.4.21.26). However, the use of prolyl-specific endoproteases for the prevention or reduction of haze in beverages has never been described or suggested.

As is typical for enzyme activities, the activity of prolyl-specific endoproteases is dependent on the pH. In a preferred embodiment of the method according to the invention, an endoprotease is added to the beverage having a maximum prolyl specific activity at a pH which corresponds to the pH of the beverage it is added to. Preferred beverages are protein containing beverages. In another preferred embodiment, the beverage contains proteins and polyphenols. Preferred beverages are beverages having a pH value below 7.

The method according to the invention is advantageously applied to beer, wine and fruit juice. It may also advantageously be applied to alcoholic beverages other than beer and wine.

The term "beer" as used herein is intended to cover at least beer prepared from mashes prepared from unmalted cereals as well as all mashes prepared from malted cereals, and all mashes prepared from a mixture of malted and unmalted cereals. The term "beer" also covers beers prepared with adjuncts, and beers with all possible alcohol contents.

Fruit juice may be juice obtained from for example red berries, strawberries, apples, pears, tomatoes, citrus fruits, vegetables etc.

The amount of proline-specific endoprotease that is added to a beverage in the method according to the invention may vary between wide limits. In a preferred embodiment of the method according to the invention at least 150 milli-units of proline-specific endoprotease activity, whereby the activity was determined by an activity measurements using Z-Gly-Pro-pNA as a substrate, per gram protein in the beverage is added.

More preferably, at least 500 milli-units of proline-specific endoprotease is added to the beverage, and most preferably, at least 1 unit of proline-specific endoprotease is added.

A maximum amount of proline-specific endoprotease activity to be added cannot be specified. The maximum amount is for example dependent on the desired amount of haze reduction or prevention, the composition of the beverage, the pH of the beverage and the pH at which the endoprotease has its maximum activity.

A prolyl-specific endoprotease may be added at different stages during the preparation of a beverage.

During the preparation process of beer, the prolyl-specific endoprotease is advantageously added to a mash. In another embodiment, the prolyl-specific endoprotease is added to a fermented beer before haze is formed. However, it is also possible that prolyl-specific endoprotease is added to a fermented beer after haze has been formed. The prolyl-specific endoprotease may advantageously be added to the mashing or maturation step in a process for the preparation of beer.

During the preparation of wine, the prolyl-specific endoprotease is preferably added to a fermented wine. The prolyl-specific endoprotease may advantageously be added after alcoholic fermentation or after malolactic fermentation in a process for the production of a wine.

In a process for the preparation of a fruit juice, the prolyl-specific endoprotease is preferably added during the maceration or depectinization.

Since haze formation often occurs in acidic beverages such as for example beer, wine and fruit juice, prolyl-specific endoproteases having a prolyl specific activity at a pH value below 7 are preferably used. Most preferably, prolyl-specific endoproteases having a maximum prolyl specific activity at a pH value below 7 are used in the method according to the invention.

The present invention further provides an isolated polypeptide which has proline-specific endoprotease activity selected from the group consisting of:
(a) a polypeptide which has an amino acid sequence which has at least 40% overall amino acid sequence identity with SEQ ID NO: 4, SEQ ID NO: 5, OR SEQ ID NO: 7 or a fragment thereof;
(b) a polypeptide which is encoded by a polynucleotide which hybridizes with (i) the nucleic acid sequence of SEQ ID NO: 1, SEQ ID NO: 2, SEQ ID NO: 3 OR SEQ ID NO: 6 or a fragment thereof which is at least 80% or 90% identical over 60, preferably over 100 nucleotides, more preferably at least 90% identical over 200 nucleotides, or (ii) a nucleic acid sequence complementary to the nucleic acid sequence of (i)

It also provides a nucleic acid molecule encoding the prolyl-specific endoprotease.

The invention also relates to purified or isolated polypeptides having prolyl-specific endo-protease activity. Preferred are purified prolyl-specific endoproteases having a maximum activity at pH values below 7.

The invention provides an isolated polypeptide having the amino acid sequence according to SEQ ID NO: 4, SEQ ID NO: 5 or SEQ ID NO: 7, an amino acid sequence obtainable by expressing the polynucleotide sequences of SEQ ID NO: 1, SEQ ID NO: 2, SEQ ID NO: 3, OR SEQ ID NO: 6 in an appropriate host. Also, a peptide or polypeptide comprising a functional equivalent of the above polypeptides is comprised within the present invention. The above polypeptides are collectively comprised in the term "polypeptides according to the invention"

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, $2^{nd}$, ed. Cold Spring Harbor Laboratory, Cold Spring Harbor Laboratory Press, Cold Spring Harbor, N.Y., 1989)

By "isolated" or "purified" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The polypeptide according to the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

An advantageous embodiment of the invention concerns a purified or isolated polypeptide having endo-pro activity. Such purified or isolated polypeptide may be obtained from a fermentation broth wherein an organism according to the invention, such as an *A. niger* strain carrying a polynucleotide according to the invention, has been cultured. A person skilled in the art will know how to obtain at least partially purified enzyme from the supernatant of such a culture.

A particularly advantageous method of purification is the following. After culturing the cells in an appropriate fermentation broth, the cells were separated from the culture supernatant by centrifugation. The supernatant had a hazy look. Larger particles remaining in the supernatant were then subsequently removed by filtration with 0.5% Dicalite or preferably 1.0% Dicalite in order to prevent clogging of the filter that is applied in the next step. Next, Germ reduction filtration was applied to decrease the amount of germs in the solution. Still, the filtrate was not clear. A Millipore filter with a Molecular weight cut-off value of 10 k Dalton was subsequently used for further reduction of water, salt and sugar content of the solution. A pressure of 1 bar was applied over the filter. Typical yields obtained were between 50 and 92% based on units present in the fermentation broth versus units obtained in the purified ultrafiltrate. Typical concentrations of enzyme in the ultrafiltrate result in an prolyl-specific endoprotease activity in the range of 4 to 10 Units per ml.

Further purification was obtained by applying either of the following methods:

Lab-scale purification was performed using the Akta Explorer on a 24 ml Q-sepharose FF column (bed height 12 cm/diameter 1.6 cm). 10 ml UF-concentrate was diluted 10 times in buffer A and applied to the column. Proteins were eluted in a gradient: 0 to 50% B in 20 CV. Buffer A was 20 mM NaAc pH 5.1. Buffer B was 20 mM NaAc+1 M NaCl pH 5.1. Flow was 5 ml/min.

Purification was performed using the Akta purifier according to work instruction W-0894.A on a 500 ml Q-sepharose FF column (bed height 23.5 cm/diameter 5 cm). 200 ml UF-concentrate was diluted 10 times in buffer A and applied to the column. Proteins were eluted in a gradient: 0 to 40% B in 20 CV. Buffer A was 20 mM NaAc pH 5.1. Buffer B was 20 mM NaAc+1 M NaCl pH 5.1. Flow was 10 ml/min. Fractions were manually collected.

The obtained product exhibited a single peak on HPSEC and appeared as a single band in SDS PAGE and IEF. It may thus be concluded that prolyl-specific endoprotease may be purified to homogeneity using Q-sepharose FF. Estimated purity was over 90% and specific activity on Z-gly-Pro-pNA was at least 0.094 U/mg.

Polypeptides of the invention may be in an isolated form. It will be understood that the polypeptide may be mixed with carriers or diluents which will not interfere with the intended purpose of the polypeptide and still be regarded as isolated. A polypeptide of the invention may also be in a more substantially purified form, in which case it will generally comprise the polypeptide in a preparation in which more than 70%. e.g. more than 80%, 90%, 95%, 98% or 99% of the proteins in the preparation is a polypeptide of the invention.

Polypeptides of the invention may be provided in a form such that they are outside their natural cellular environment. Thus, they may be substantially isolated or purified, as discussed above, or in a cell in which they do not occur in nature, for example a cell of other fungal species, animals, plants or bacteria.

Advantageously, isolated or purified prolyl-specific endoprotease are used in the method according to the invention.

An isolated or purified proline-specific endoprotease according to the invention preferably has at least 10 units of proline specific endoprotease activity per gram of proteinaceous material. These units should be measured using the synthetic peptide Z-Gly-Pro-pNA at 37 degrees C. and pH 5, as described in the Methods section.

Proline-specific endoproteases are widely found in animals and plants, but their presence in microorganisms appears to be limited. To date, proline-specific endoprotease have been identified in species of *Aspergillus* (EP 0 522 428), *Flavobacterium* (EP 0 967 285) and *Aeromonas* (J. Biochem. 113, 790-796), *Xanthomonas* and *Bacteroides*. Though the proline-specific enzymes from most of these organisms are active around pH 8, the *Aspergillus* enzyme is optimally active around pH 5. The proline-specific endoprotease of the invention may be isolated from one of the above-mentioned microbial species, particularly from a species of *Aspergillus*. Preferably, the proline-specific endoprotease is isolated from a strain of *Aspergillus niger*. More preferably, the proline-specific endoprotease is isolated from an *Aspergillus niger* host engineered to overexpress a gene encoding a proline-specific endoprotease, although other hosts, such as *E. coli* are suitable expression vectors. For example, the cloning and overproduction of the *Flavobacterium* derived proline-specific endoprotease in, amongst others, *E. coli* has made certain proline-specific endoproteases available in a pure form. An example of such an overproducing construct is provided in the World Journal of Microbiology & Biotechnology, Vol 11, pp 209-212. An *Aspergillus niger* host is preferably used to produce a non-recombinant self-construct utilizing *A. niger* promoters to drive the expression of a gene encoding an *A. niger* proline-specific endoprotease.

In a first embodiment, the present invention provides an isolated polypeptide having an amino acid sequence which has an overall degree of amino acid sequence identity to amino acids of SEQ ID NO: 4, SEQ ID NO: 5, OR SEQ ID NO: 7 (i.e. the polypeptide) of at least about 40%, preferably at least about 50%, preferably at least about 60%, preferably at least about 65%, preferably at least about 70%, more preferably at least about 80%, even more preferably at least about 90%, still more preferably at least about 95%, and most preferably at least about 97%, and which has proline specific endoprotease activity.

For the purposes of the present invention, the degree of identity between two or more amino acid sequences is determined by BLAST P protein database search program (Altschul et al., 1997, Nucleic Acids Research 25: 3389-3402) with matrix Blosum 62 and an expected threshold of 10.

A polypeptide of the invention may comprise the amino acid sequence set forth in SEQ ID NO: 4, SEQ ID NO: 5, OR SEQ ID NO: or a substantially homologous sequence, or a fragment of either sequence having proline specific endoprotease activity. In general, the naturally occurring amino acid sequence shown in SEQ ID NO: 4, SEQ ID NO: 5, OR SEQ ID NO: 7 is preferred.

The polypeptide of the invention may also comprise a naturally occurring variant or species homologue of the polypeptide of SEQ ID NO: 4, SEQ ID NO: 5, OR SEQ ID NO: 7.

A variant is a polypeptide that occurs naturally in, for example, fungal, bacterial, yeast or plant cells, the variant having proline specific endoprotease activity and a sequence substantially similar to the protein of SEQ ID NO: 4, SEQ ID NO: 5, OR SEQ ID NO: 7. The term "variants" refers to polypeptides which have the same essential character or basic biological functionality as the proline specific endoprotease of SEQ ID NO: 4, SEQ ID NO: 5, OR SEQ ID NO: 7, and includes allelic variants. Preferably, a variant polypeptide has at least the same level of proline specific endoprotease activity as the polypeptide of SEQ ID NO: 4, SEQ ID NO: 5, OR SEQ ID NO: 7. Variants include allelic variants either from the same strain as the polypeptide of SEQ ID NO: 4, SEQ ID NO: 5, OR SEQ ID NO: 7. or from a different strain of the same genus or species.

Similarly, a species homologue of the inventive protein is an equivalent protein of similar sequence which is an proline specific endoprotease and occurs naturally in another species of *Aspergillus*.

Variants and species homologues can be isolated using the procedures described herein which were used to isolate the polypeptide of SEQ ID NO: 4, SEQ ID NO: 5, OR SEQ ID NO: 7 and performing such procedures on a suitable cell source, for example a bacterial, yeast, fungal or plant cell. Also possible is to use a probe of the invention to probe libraries made from yeast, bacterial, fungal or plant cells in order to obtain clones expressing variants or species homologues of the polypeptide of SEQ ID NO: 4, SEQ ID NO: 5, OR SEQ ID NO: 7. These clones can be manipulated by conventional techniques to generate a polypeptide of the invention which thereafter may be produced by recombinant or synthetic techniques known per se.

The sequence of the polypeptide of SEQ ID NO: 4, SEQ ID NO: 5, OR SEQ ID NO: 7 and of variants and species homologues can also be modified to provide polypeptides of the invention. Amino acid substitutions may be made, for example from 1, 2 or 3 to 10, 20 or 30 substitutions. The same number of deletions and insertions may also be made. These changes may be made outside regions critical to the function of the polypeptide, as such a modified polypeptide will retain its proline specific endoprotease activity.

Polypeptides of the invention include fragments of the above mentioned full length polypeptides and of variants thereof, including fragments of the sequence set out in SEQ ID NO: 4, SEQ ID NO: 5, OR SEQ ID NO: 7. Such fragments will typically retain activity as a proline specific endoprotease. Fragments may be at least 50, 100 or 200 amino acids long or may be this number of amino acids short of the full length sequence shown in SEQ ID NO: 4, SEQ ID NO: 5, OR SEQ ID NO: 7.

Polypeptides of the invention can, if necessary, be produced by synthetic means although usually they will be made recombinantly as described below. Synthetic polypeptides may be modified, for example, by the addition of histidine residues or a T7 tag to assist their identification or purification, or by the addition of a signal sequence to promote their secretion from a cell.

Thus, the variants sequences may comprise those derived from strains of *Aspergillus* other than the strain from which the polypeptide of SEQ ID NO: 4, SEQ ID NO: 5, OR SEQ ID NO: 7 was isolated. Variants can be identified from other *Aspergillus* strains by looking for proline specific endoprotease activity and cloning and sequencing as described herein. Variants may include the deletion, modification or addition of single amino acids or groups of amino acids within the protein sequence, as long as the peptide maintains the basic biological functionality of the proline specific endoprotease of SEQ ID NO: 4, SEQ ID NO: 5, OR SEQ ID NO: 7.

Amino acid substitutions may be made, for example from 1, 2 or from 3 to 10, 20 or 30 substitutions. The modified polypeptide will generally retain activity as an proline specific endoprotease. Conservative substitutions may be made; such substitutions are well known in the art. Preferably substitutions do not affect the folding or activity of the polypeptide.

Shorter polypeptide sequences are within the scope of the invention. For example, a peptide of at least 50 amino acids or up to 60, 70, 80, 100, 150 or 200 amino acids in length is considered to fall within the scope of the invention as long as it demonstrates the basic biological functionality of the proline specific endoprotease of SEQ ID NO: 4, SEQ ID NO: 5, OR SEQ ID NO: 7. In particular, but not exclusively, this aspect of the invention encompasses the situation in which the protein is a fragment of the complete protein sequence.

In a second embodiment, the present invention provides an to isolated polypeptide which has proline specific endoprotease activity, and is encoded by polynucleotides which hybridize or are capable of hybrizing under low stringency conditions, more preferably medium stringency conditions, and most preferably high stringency conditions, with (I) the nucleic acid sequence of SEQ ID NO: 1, SEQ ID NO: 2, SEQ ID NO: 3 OR SEQ ID NO: 6 or a nucleic acid fragment comprising at least the c-terminal portion of SEQ ID NO: 1, SEQ ID NO: 2, SEQ ID NO: 3 OR SEQ ID NO: 6, but having less than all or having bases differing from the bases of SEQ ID NO: 1, SEQ ID NO: 2, SEQ ID NO: 3 OR SEQ ID NO: 6; or (ii) with a nucleic acid strand complementary to SEQ ID NO: 1, SEQ ID NO: 2, SEQ ID NO: 3 OR SEQ ID NO: 6.

The term "capable of hybridizing" means that the target polynucleotide of the invention can hybridize to the nucleic acid used as a probe (for example, the nucleotide sequence set forth in SEQ. ID NO: 1, SEQ ID NO: 2, SEQ ID NO: 3 OR SEQ ID NO: 6, or a fragment thereof, or the complement of SEQ ID NO: 1, SEQ ID NO: 2, SEQ ID NO: 3 OR SEQ ID NO: 6) at a level significantly above background. The invention also includes the polynucleotides that encode the proline specific endoprotease of the invention, as well as nucleotide sequences which are complementary thereto. The nucleotide sequence may be RNA or DNA, including genomic DNA, synthetic DNA or cDNA. Preferably, the nucleotide sequence is DNA and most preferably, a genomic DNA sequence. Typically, a polynucleotide of the invention comprises a contiguous sequence of nucleotides which is capable of hybridizing under selective conditions to the coding sequence or the complement of the coding sequence of SEQ ID NO: 1, SEQ ID NO: 2, SEQ ID NO: 3 OR SEQ ID NO: 6. Such nucleotides can be synthesized according to methods well known in the art.

A polynucleotide of the invention can hybridize to the coding sequence or the complement of the coding sequence of SEQ ID NO: 1, SEQ ID NO: 2, SEQ ID NO: 3 OR SEQ ID NO: 6 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1, SEQ ID NO: 2, SEQ ID NO: 3 OR SEQ ID NO: 6 is typically at least 10 fold, preferably at least 20 fold, more preferably at least 50 fold, and even more preferably at least 100 fold, as intense as interactions between other polynucleotides and the coding sequence of SEQ ID NO: 1, SEQ ID NO: 2, SEQ ID NO: 3 OR SEQ ID NO: 6. The intensity of interaction may be measured, for example, by radiolabelling the probe, for example with $^{32}P$. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.).

Modifications

Polynucleotides of the invention may comprise DNA or RNA. They may be single or double stranded. They may also be polynucleotides which include within them synthetic or modified nucleotides including peptide nucleic acids. A number of different types of modifications to polynucleotides are known in the art. These include a methylphosphonate and phosphorothioate backbones, and addition of acridine or polylysine chains at the 3' and/or 5' ends of the molecule. For the purposes of the present invention, it is to be understood that the polynucleotides described herein may be modified by any method available in the art.

It is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The coding sequence of SEQ ID NO: 1, SEQ ID NO: 2, SEQ ID NO: 3 OR SEQ ID NO: 6 may be modified by nucleotide substitutions, for example from 1, 2 or 3 to 10, 25, 50 or 100 substitutions. The polynucleotide of SEQ ID NO: 1, SEQ ID NO: 2, SEQ ID NO: 3 OR SEQ ID NO: 6 may alternatively or additionally be modified by one or more insertions and/or deletions and/or by an extension at either or both ends. The modified polynucleotide generally encodes a polypeptide which has proline specific endoprotease activity. Degenerate substitutions may be made and/or substitutions may be made which would result in a conservative amino acid substitution when the modified sequence is translated, for example as discussed with reference to polypeptides later.

Homologues

A nucleotide sequence which is capable of selectively hybridizing to the complement of the DNA coding sequence of SEQ ID NO: 1, SEQ ID NO: 2, SEQ ID NO: 3 OR SEQ ID NO: 6 is included in the invention and will generally have at least 50% or 60%, at least 70%, at least 80%, at least 90%, at least 95%, at least 98% or at least 99% sequence identity to the coding sequence of SEQ ID NO: 1, SEQ ID NO: 2, SEQ ID NO: 3 OR SEQ ID NO: 6 over a region of at least 60, preferably at least 100, more preferably at least 200 contiguous nucleotides or most preferably over the full length of SEQ ID NO: 1, SEQ ID NO: 2, SEQ ID NO: 3 OR SEQ ID NO: 6. Likewise, a nucleotide which encodes an active proline specific endoprotease and which is capable of selectively hybridizing to a fragment of a complement of the DNA coding sequence of SEQ ID NO: 1, SEQ ID NO: 2, SEQ ID NO: 3 OR SEQ ID NO: 6, is also embraced by the invention. A C-terminal fragment of the nucleic acid sequence of SEQ ID NO: 1, SEQ ID NO: 2, SEQ ID NO: 3 OR SEQ ID NO: 6 which is at least 80% or 90% identical over 60, preferably over 100 nucleotides, more preferably at least 90% identical over 200 nucleotides is encompassed by the invention.

Any combination of the above mentioned degrees of identity and minimum sizes may be used to define polynucleotides of the invention, with the more stringent combinations (i.e. higher identity over longer lengths) being preferred. Thus, for example, a polynucleotide which is at least 80% or 90% identical over 60, preferably over 100 nucleotides, forms one aspect of the invention, as does a polynucleotide which is at least 90% identical over 200 nucleotides.

The UWGCG Package provides the BESTFIT program which may be used to calculate identity (for example used on its default settings).

The PILEUP and BLAST N algorithms can also be used to calculate sequence identity or to line up sequences (such as identifying equivalent or corresponding sequences, for example on their default settings).

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold. These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix alignments (B) of 50, expectation (E) of 10, M=5, N=4, and a comparison of both strands.

The BLAST algorithm performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Primers and Probes

Polynucleotides of the invention include and may be used as primers, for example as polymerase chain reaction (PCR) primers, as primers for alternative amplification reactions, or as probes for example labelled with a revealing label by conventional means using radioactive or non-radioactive labels, or the polynucleotides may be cloned into vectors. Such primers, probes and other fragments will be at least 15, for example at least 20, 25, 30 or 40 nucleotides in length. They will typically be up to 40, 50, 60, 70, 100, 150, 200 or 300 nucleotides in length, or even up to a few nucleotides (such as 5 or 10 nucleotides) short of the coding sequence of SEQ ID NO: 1, SEQ ID NO: 2, SEQ ID NO: 3 OR SEQ ID NO: 6.

In general, primers will be produced by synthetic means, involving a step-wise manufacture of the desired nucleic acid sequence one nucleotide at a time. Techniques for accomplishing this using automated protocols are readily available in the art. Longer polynucleotides will generally be produced using recombinant means, for example using PCR cloning techniques. This will involve making a pair of primers (typically of about 15-30 nucleotides) to amplify the desired region of the proline specific endoprotease to be cloned, bringing the primers into contact with mRNA, cDNA or genomic DNA obtained from a yeast, bacterial, plant, prokaryotic or fungal cell, preferably of an *Aspergillus* strain, performing a polymerase chain reaction under conditions suitable for the amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the polynucleotides encoding the proline specific endoprotease sequences described herein. Introns, promoter and trailer regions are within the scope of the invention and may also be obtained in an analogous manner (e.g. by recombinant means, PCR or cloning techniques), starting with genomic DNA from a fungal, yeast, bacterial plant or prokaryotic cell.

The polynucleotides or primers may carry a revealing label. Suitable labels include radioisotopes such as $^{32}P$ or $^{35}S$, enzyme labels, or other protein labels such as biotin. Such labels may be added to polynucleotides or primers of the invention and may be detected using techniques known to persons skilled in the art.

Polynucleotides or primers (or fragments thereof) labelled or unlabelled may be used in nucleic acid-based tests for detecting or sequencing an proline specific endoprotease or a variant thereof in a fungal sample. Such detection tests will generally comprise bringing a fungal sample suspected of containing the DNA of interest into contact with a probe comprising a polynucleotide or primer of the invention under hybridizing conditions, and detecting any duplex formed between the probe and nucleic acid in the sample. Detection may be achieved using techniques such as PCR or by immobilizing the probe on a solid support, removing any nucleic acid in the sample which is not hybridized to the probe, and then detecting any nucleic acid which is hybridized to the probe. Alternatively, the sample nucleic acid may be immobilized on a solid support, the probe hybridized and the amount of probe bound to such a support after the removal of any unbound probe detected.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like. The probes and polynucleotides of the invention may also be used in microassay.

Preferably, the polynucleotide of the invention is obtainable from the same organism as the polypeptide, such as a fungus, in particular a fungus of the genus *Aspergillus*.

The polynucleotides of the invention also include variants of the sequence of SEQ ID NO: 1, SEQ ID NO: 2, SEQ ID NO: 3 OR SEQ ID NO: 6 which encode for a polypeptide having proline specific endoprotease activity. Variants may be formed by additions, substitutions and/or deletions. Such variants of the coding sequence of SEQ ID NO: 1, SEQ ID NO: 2, SEQ ID NO: 3 OR SEQ ID NO: 6 may thus encode polypeptides which have the ability to digest a polypeptide chain at the carboxyterminal side of proline.

Production of Polynucleotides

Polynucleotides which do not have 100% identity with SEQ ID NO: 1, SEQ ID NO: 2, SEQ ID NO: 3 OR SEQ ID NO: 6 but fall within the scope of the invention can be obtained in a number of ways. Thus, variants of the proline specific endoprotease sequence described herein may be obtained for example, by probing genomic DNA libraries made from a range of organisms, such as those discussed as sources of the polypeptides of the invention. In addition, other fungal, plant or prokaryotic homologues of proline specific endoprotease may be obtained and such homologues and fragments thereof in general will be capable of hybridising to SEQ ID NO: 1, SEQ ID NO: 2, SEQ ID NO: 3 OR SEQ ID NO: 6. Such sequences may be obtained by probing cDNA libraries or genomic DNA libraries from other species, and probing such libraries with probes comprising all or part of SEQ ID. 1 under conditions of low, medium to high stringency (as described earlier). Nucleic acid probes comprising all or part of SEQ ID NO: 1, SEQ ID NO: 2, SEQ ID NO: 3 OR SEQ ID NO: 6 may be used to probe cDNA or genomic libraries from other species, such as those described as sources for the polypeptides of the invention.

Species homologues may also be obtained using degenerate PCR, which uses primers designed to target sequences within the variants and homologues which encode conserved amino acid sequences. The primers can contain one or more degenerate positions and will be used at stringency conditions lower than those used for cloning sequences with single sequence primers against known sequences.

Alternatively, such polynucleotides may be obtained by site directed mutagenesis of the proline specific endoprotease sequences or variants thereof. This may be useful where, for example, silent codon changes to sequences are required to optimize codon preferences for a particular host cell in which the polynucleotide sequences are being expressed. Other sequence changes may be made in order to introduce restriction enzyme recognition sites, or to alter the property or function of the polypeptides encoded by the polynucleotides.

The invention includes double stranded polynucleotides comprising a polynucleotide of the invention and its complement.

The present invention also provides polynucleotides encoding the polypeptides of the invention described above. Since such polynucleotides will be useful as sequences for recombinant production of polypeptides of the invention, it is not necessary for them to be capable of hybridising to the sequence of SEQ ID NO: 1, SEQ ID NO: 2, SEQ ID NO: 3 OR SEQ ID NO: 6, although this will generally be desirable. Otherwise, such polynucleotides may be labelled, used, and made as described above if desired.

Recombinant Polynucleotides.

The invention also provides vectors comprising a polynucleotide of the invention, including cloning and expression vectors, and in another aspect methods of growing, transforming or transfecting such vectors into a suitable host cell, for example under conditions in which expression of a polypeptide of, or encoded by a sequence of, the invention occurs. Provided also are host cells comprising a polynucleotide or vector of the invention wherein the polynucleotide is heterologous to the genome of the host cell. The term "heterologous", usually with respect to the host cell, means that the polynucleotide does not naturally occur in the genome of the host cell or that the polypeptide is not naturally produced by that cell. Preferably, the host cell is a yeast cell, for example a yeast cell of the genus *Kluyveromyces* or *Saccharomyces* or a filamentous fungal cell, for example of the genus *Aspergillus*.

Polynucleotides of the invention can be incorporated into a recombinant replicable vector, for example a cloning or expression vector. The vector may be used to replicate the nucleic acid in a compatible host cell. Thus, in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Vectors

The vector into which the expression cassette of the invention is inserted may be any vector that may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, such as a plasmid. Alternatively, the vector may be one which, when introduced into a host cell, is integrated into the host cell genome and replicates together with the chromosome(s) into which it has been integrated.

Preferably, when a polynucleotide of the invention is in a vector it is operably linked to a regulatory sequence which is capable of providing for the expression of the coding sequence by the host cell. i.e. the vector is an expression vector. The term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under conditions compatible with the control sequences.

The vectors may, for example in the case of plasmid, cosmid, virus or phage vectors, be provided with an origin of replication, optionally a promoter for the expression of the polynucleotide and optionally an enhancer and/or a regulator of the promoter. A terminator sequence may be present, as may be a polyadenylation sequence. The vectors may contain one or more selectable marker genes, for example an ampicillin resistance gene in the case of a bacterial plasmid or a neomycin resistance gene for a mammalian vector. Vectors may be used in vitro, for example for the production of RNA or can be used to transfect or transform a host cell.

The DNA sequence encoding the polypeptide is preferably introduced into a suitable host as part of an expression construct in which the DNA sequence is operably linked to expression signals which are capable of directing expression of the DNA sequence in the host cells. For transformation of the suitable host with the expression construct transformation procedures are available which are well known to the skilled person. The expression construct can be used for transformation of the host as part of a vector carrying a selectable marker, or the expression construct is co-transformed as a separate molecule together with the vector carrying a selectable marker. The vectors may contain one or more selectable marker genes.

Preferred selectable markers include but are not limited to those that complement a defect in the host cell or confer resistance to a drug. They include for example versatile marker genes that can be used for transformation of most filamentous fungi and yeasts such as acetamidase genes or cDNAs (the amdS, niaD, facA genes or cDNAs from *A. nidulans, A. oryzae*, or *A. niger*), or genes providing resistance to antibiotics like G418, hygromycin, bleomycin, kanamycin, phleomycin or benomyl resistance (benA). Alternatively, specific selection markers can be used such as auxotrophic markers which require corresponding mutant host strains: e.g. URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase subunit 9 (oliC), orotidine-5'-phosphate-decarboxylase (pvrA), the bacterial G418 resistance gene (useful in yeast, but not in filamentous fungi), the ampicillin resistance gene (*E. coli*), the neomycin resistance gene (*Bacillus*) and the *E. coli* uidA gene, coding for glucuronidase (GUS). Vectors may be used in vitro, for example for the production of RNA or to transfect or transform a host cell.

For most filamentous fungi and yeast, the expression construct is preferably integrated into the genome of the host cell in order to obtain stable transformants. However, for certain yeasts suitable episomal vector systems are also available into which the expression construct can be incorporated for stable and high level expression. Examples thereof include vectors derived from the 2 μm, CEN and pKD1 plasmids of *Saccharomyces* and *Kluyveromyces*, respectively, or vectors containing an AMA sequence (e.g. AMA1 from *Aspergillus*). When expression constructs are integrated into host cell genomes, the constructs are either integrated at random loci in the genome, or at predetermined target loci using homologous recombination, in which case the target loci preferably comprise a highly expressed gene. A highly expressed gene is a gene whose mRNA can make up at least 0.01% (w/w) of the total cellular mRNA, for example under induced conditions, or alternatively, a gene whose gene product can make up at least 0.2% (w/w) of the total cellular protein, or, in case of a secreted gene product, can be secreted to a level of at least 0.05 g/l.

An expression construct for a given host cell will usually contain the following elements operably linked to each other in consecutive order from the 5'-end to 3'-end relative to the coding strand of the sequence encoding the polypeptide of the first aspect: (1) a promoter sequence capable of directing transcription of the DNA sequence encoding the polypeptide in the given host cell, (2) preferably, a 5'-untranslated region (leader), (3) optionally, a signal sequence capable of directing secretion of the polypeptide from the given host cell into the culture medium, (4) the DNA sequence encoding a mature and preferably active form of the polypeptide, and preferably also (5) a transcription termination region (terminator) capable of terminating transcription downstream of the DNA sequence encoding the polypeptide.

Downstream of the DNA sequence encoding the polypeptide, the expression construct preferably contains a 3' untranslated region containing one or more transcription termination sites, also referred to as a terminator. The origin of the terminator is less critical. The terminator can for example be native to the DNA sequence encoding the polypeptide. However, preferably a yeast terminator is used in yeast host cells and a filamentous fungal terminator is used in filamentous fungal host cells. More preferably, the terminator is endogenous to the host cell in which the DNA sequence encoding the polypeptide is expressed.

Enhanced expression of the polynucleotide encoding the polypeptide of the invention may also be achieved by the selection of heterologous regulatory regions, e.g. promoter, signal sequence and terminator regions, which serve to increase expression and, if desired, secretion levels of the protein of interest from the chosen expression host and/or to provide for the inducible control of the expression of the polypeptide of the invention.

Aside from the promoter native to the gene encoding the polypeptide of the invention, other promoters may be used to direct expression of the polypeptide of the invention. The promoter may be selected for its efficiency in directing the expression of the polypeptide of the invention in the desired expression host.

Promoters/enhancers and other expression regulation signals may be selected to be compatible with the host cell for which the expression vector is designed. For example prokaryotic promoters may be used, in particular those suitable for use in *E. coli* strains. When expression of the polypeptides of the invention is carried out in mammalian cells, mammalian promoters may be used. Tissues-specific promoters, for example hepatocyte cell-specific promoters, may also be used. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, herpes simplex virus promoters or adenovirus promoters.

Suitable yeast promoters include the *S. cerevisiae* GAL4 and ADH promoters and the *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as β-actin promoters, may be used. Tissue-specific promoters, in particular endothelial or neuronal cell specific promoters (for example the DDAHI and DDAHII promoters), are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

A variety of promoters can be used that are capable of directing transcription in the host cells of the invention. Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which are preferred for use in fungal expression hosts are those which are obtainable from the fungal genes for xylanase (xlnA), phytase, ATP-synthetase subunit 9 (oliC), triose phosphate isomerase (tpi), alcohol dehydrogenase (AdhA), amylase (amy), amyloglucosidase (AG—from the glaA gene), acetamidase (amdS) and glyceraldehyde-3-phosphate dehydrogenase (gpd) promoters.

Examples of strong yeast promoters which may be used include those obtainable from the genes for alcohol dehydrogenase, lactase, 3-phosphoglycerate kinase and triosephosphate isomerase.

Examples of strong bacterial promoters which may be used include the amylase and SPo2 promoters as well as promoters from extracellular protease genes.

Promoters suitable for plant cells which may be used include napaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters.

The vector may further include sequences flanking the polynucleotide giving rise to RNA which comprise sequences homologous to ones from eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses (such as HPV-16 or HPV-18). Gene transfer techniques using these viruses are known to those skilled in the art. Retrovirus vectors for example may be used to stably integrate the polynucleotide giving rise to the antisense RNA into the host genome. Replication-defective adenovirus vectors by contrast remain episomal and therefore allow transient expression.

The vector may contain a polynucleotide of the invention oriented in an antisense direction to provide for the production of antisense RNA. This may be used to reduce, if desirable, the levels of expression of the polypeptide.

Host Cells and Expression

In a further aspect the invention provides a process for preparing a polypeptide of the invention which comprises cultivating a host cell transformed or transfected with an expression vector as described above under conditions suitable for expression by the vector of a coding sequence encoding the polypeptide, and recovering the expressed polypeptide. Polynucleotides of the invention can be incorporated into a recombinant replicable vector, such as an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell. Suitable host cells include bacteria such as *E. coli*, yeast, mammalian cell lines and other eukaryotic cell lines, for example insect cells such as Sf9 cells and (e.g. filamentous) fungal cells.

Preferably the polypeptide is produced as a secreted protein in which case the DNA sequence encoding a mature form of the polypeptide in the expression construct is operably linked to a DNA sequence encoding a signal sequence. In the case where the gene encoding the secreted protein has in the wild type strain a signal sequence preferably the signal sequence used will be native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast MFalpha genes. Similarly, a suitable signal sequence for filamentous fungal host cells is e.g. a signal sequence derived from a filamentous fungal amyloglucosidase (AG) gene, e.g. the *A. niger* glaA gene. This signal sequence may be used in combination with the amyloglucosidase (also called (gluco)amylase) promoter itself, as well as in combination with other promoters. Hybrid signal sequences may also be used within the context of the present invention.

Preferred heterologous secretion leader sequences are those originating from the fungal amyloglucosidase (AG) gene (glaA—both 18 and 24 amino acid versions e.g. from *Aspergillus*), the MFalpha gene (yeasts e.g. *Saccharomyces* and *Kluyveromyces*) or the alpha-amylase gene (*Bacillus*).

The vectors may be transformed or transfected into a suitable host cell as described above to provide for expression of a polypeptide of the invention. This process may comprise culturing a host cell transformed with an expression vector as described above under conditions suitable for expression of the polypeptide, and optionally recovering the expressed polypeptide.

A further aspect of the invention thus provides host cells transformed or transfected with or comprising a polynucleotide or vector of the invention. Preferably the polynucleotide is carried in a vector which allows the replication and expression of the polynucleotide. The cells will be chosen to be compatible with the said vector and may for example be prokaryotic (for example bacterial), or eukaryotic fungal, yeast or plant cells.

The invention encompasses processes for the production of a polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is herein defined as a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over filamentous fungal cells because they are easier to manipulate. However, some proteins are either poorly secreted from yeasts, or in some cases are not processed properly (e.g. hyperglycosylation in yeast). In these instances, a filamentous fungal host organism should be selected.

Bacteria from the genus *Bacillus* are very suitable as heterologous hosts because of their capability to secrete proteins into the culture medium. Other bacteria suitable as hosts are those from the genera *Streptomyces* and *Pseudomonas*. A preferred yeast host cell for the expression of the DNA sequence encoding the polypeptide is one of the genus *Saccharomyces, Kluyveromyces, Hansenula, Pichia, Yarrowia*, or *Schizosaccharomyces*. More preferably, a yeast host cell is selected from the group consisting of the species *Saccharomyces cerevisiae, Kluyveromyces lactis* (also known as *Kluyveromyces marxianus* var. *lactis*), *Hansenula polymorpha, Pichia pastoris, Yarrowia lipolytica*, and *Schizosaccharomyces pombe*.

Most preferred for the expression of the DNA sequence encoding the polypeptide are, however, filamentous fungal host cells. Preferred filamentous fungal host cells are selected from the group consisting of the genera *Aspergillus, Trichoderma, Fusarium, Disporotrichum, Penicillium, Acremonium, Neurospora, Thermoascus, Myceliophtora, Sporotrichum, Thielavia*, and *Talaromyces*. More preferably a filamentous fungal host cell is of the species *Aspergillus oyzae, Aspergillus sojae* or *Aspergillus nidulans* or is of a species from the *Aspergillus niger* Group (as defined by Raper and Fennell, The Genus *Aspergillus*, The Williams & Wilkins Company, Baltimore, pp 293-344, 1965). These include but are not limited to *Aspergillus niger, Aspergillus awamori, Aspergillus tubigensis, Aspergillus aculeatus, Aspergillus foetidus, Aspergillus nidulans, Aspergillus japonicus, Aspergillus oryzae* and *Aspergillus ficuum*, and also those of the species *Trichoderma reesei, Fusarium graminearum, Penicillium chrysogenum, Acremonium alabamense, Neurospora crassa, Myceliophtora thermophilum, Sporotrichum cellulophilum, Disporotrichum dimorphosporum* and *Thielavia terrestris*.

Examples of preferred expression hosts within the scope of the present invention are fungi such as *Aspergillus* species (in particular those described in EP-A-184,438 and EP-A-284,603) and *Trichoderma* species; bacteria such as *Bacillus* species (in particular those described in EP-A-134,048 and EP-A-253,455), especially *Bacillus subtilis, Bacillus licheniformis, Bacillus amyloliquefaciens, Pseudomonas* species; and yeasts such as *Kluyveromyces* species (in particular those described in EP-A-096,430 such as *Kluyveromyces lactis* and in EP-A-301,670) and *Saccharomyces* species, such as *Saccharomyces cerevisiae*.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (typically stably) into its genome a sequence encoding the polypeptides of the invention. The transformation of plant cells can be performed using known techniques, for example using a Ti or a Ri plasmid from *Agrobacterium tumefaciens*. The plasmid (or vector) may thus contain sequences necessary to infect a plant, and derivatives of the Ti and/or Ri plasmids may be employed.

The host cell may overexpress the polypeptide, and techniques for engineering over-expression are well known and can be used in the present invention. The host may thus have two or more copies of the polynucleotide.

Alternatively, direct infection of a part of a plant, such as a leaf, root or stem can be effected. In this technique the plant to be infected can be wounded, for example by cutting the plant with a razor, puncturing the plant with a needle or rubbing the plant with an abrasive. The wound is then innoculated with the *Agrobacterium*. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.

Culture of Host Cells and Recombinant Production

The invention also includes cells that have been modified to express the proline specific endoprotease or a variant thereof. Such cells include transient, or preferably stably modified higher eukaryotic cell lines, such as mammalian cells or insect cells, lower eukaryotic cells, such as yeast and filamentous fungal cells or prokaryotic cells such as bacterial cells.

It is also possible for the polypeptides of the invention to be transiently expressed in a cell line or on a membrane, such as for example in a baculovirus expression system. Such systems, which are adapted to express the proteins according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culturing is ceased and the polypeptide is recovered using known procedures.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (dependent on the expression construct used) may be included or subsequently be added.

The selection of the appropriate medium may be based on the choice of expression host and/or based on the regulatory requirements of the expression construct. Suitable media are well-known to those skilled in the art. The medium may, if desired, contain additional components favoring the transformed expression hosts over other potentially contaminating microorganisms.

The fermentation may be performed over a period of from 0.5-30 days. Fermentation may be a batch, continuous or fed-batch process, at a suitable temperature in the range of between 0° C. and 45° C. and, for example, at a pH from 2 to 10. Preferred fermentation conditions include a temperature in the range of between 20° C. and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means. The proline specific endoprotease of the invention can be purified from fungal mycelium or from the culture broth into which the proline specific endoprotease is released by the cultured fungal cells.

In a preferred embodiment the polypeptide is obtained from a fungus more preferably from an *Aspergillus*, most preferably from *Aspergillus niger*.

Modifications

Polypeptides of the invention may be chemically modified, e.g. post-translationally modified. For example, they may be glycosylated (one or more times) or comprise modified amino acid residues. They may also be modified by the addition of histidine residues to assist their purification or by the addition of a signal sequence to promote secretion from the cell. The polypeptide may have amino- or carboxyl-terminal extensions, such as an amino-terminal methionine residue, a small linker peptide of up to about 20-25 residues, or a small extension that facilitates purification, such as a poly-histidine tract, an antigenic epitope or a binding domain.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

The polypeptides may be modified to include non-naturally occurring amino acids or to increase the stability of the polypeptide. When the proteins or peptides are produced by synthetic means, such amino acids may be introduced during production. The proteins or peptides may also be modified following either synthetic or recombinant production.

The polypeptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with $NaBH_4$, amidination with methylacetimidate or acylation with acetic anhydride.

The sequences provided by the present invention may also be used as starting materials for the construction of "second generation" enzymes. "Second generation" proline specific proteases are proline specific proteases, altered by mutagenesis techniques (e.g. site-directed mutagenesis), which have properties that differ from those of wild-type proline specific protease or recombinant proline specific proteases such as those produced by the present invention. For example, their temperature or pH optimum, specific activity, substrate affinity or thermostability may be altered so as to be better suited for use in a particular process.

Amino acids essential to the activity of the proline specific endoprotease of the invention, and therefore preferably subject to substitution, may be identified according to procedures known in the art, such as site-directed mutagenesis or alanine-scanning mutagenesis. In the latter technique mutations are introduced at every residue in the molecule, and the resultant mutant molecules are tested for biological activity (e.g. proline specific endoprotease activity) to identify amino acid residues that are critical to the activity of the molecule. Sites of enzyme-substrate interaction can also be determined by analysis of crystal structure as determined by such techniques as nuclear magnetic resonance, crystallography or photo-affinity labelling.

The use of yeast and filamentous fungal host cells is expected to provide for such post-translational modifications (e.g. proteolytic processing, myristilation, glycosylation, truncation, and tyrosine, serine or threonine phosphorylation) as may be needed to confer optimal biological activity on recombinant expression products of the invention.

Preparations

Polypeptides of the invention may be in an isolated form. It will be understood that the polypeptide may be mixed with carriers or diluents which will not interfere with the intended purpose of the polypeptide and still be regarded as isolated. A polypeptide of the invention may also be in a substantially purified form, in which case it will generally comprise the polypeptide in a preparation in which more than 70%, e.g. more than 80%, 90%, 95%, 98% or 99% of the proteins in the preparation is a polypeptide of the invention.

Polypeptides of the invention may be provided in a form such that they are outside their natural cellular environment. Thus, they may be substantially isolated or purified, as discussed above, or in a cell in which they do not occur in nature, for example a cell of other fungal species, animals, plants or bacteria.

The invention also relates to the use of a prolyl-specific endoprotease in the preparation of a beverage. A prolyl-specific endoprotease is used preferably in the preparation of beer, wine or fruit juice. By the addition of a prolyl-specific endoprotease according to the method according to the invention, a reduction or prevention of haze is achieved. By adding these prolyl-specifc endoproteases, new beverage are obtained. Thus, the invention also relates to beverages obtainable by the method according to the invention. These beverages include for example beer, wine and fruit juice obtainable by a method according to the invention.

An advantage of the beverages obtainable by the method according to the invention is that these beverages have a high content of anti-oxidants. Polyphenols are anti-oxidants. Beer is usually treated with a polyphenol-removing agent to prevent the formation of haze, and as a result the beer obtained has a low antioxidant activity. The same is true for other beverages treated with poly-phenol removing agents. Beer obtainable by the method according to the invention has a higher endogenous anti-oxidant activity. Because anti-oxidants are seen as health improving ingredients, the beverages obtainable by the method according to the invention may be considered as beverages that are healthier than the same type of beverage prepared with polyphenol removing, agents, such as PVPP. It is an advantage of the method according to the invention that the color of fruit juices obtainable by the method is not or less faded than the color of fruit juices obtained after the removal of polyphenols. Wines and fruit juices obtainable by the method according to the invention have improved aroma and flavour in comparison to beverages obtained by a method wherein bentonite or a similar compound is used, since bentonite not only removes proteins but also aroma and/or flavour components.

EXAMPLES AND COMPARATIVE EXPERIMENTS

Materials

Proline-Specific Endoprotease Enzymes (Endo-Pro's)

*Aspergillus niger* G306 was deposited with the CBS (CBS109712) on 10 Sep. 2001. *A. niger* G306 contains a gene encoding a prolyl-specific endoprotease according to the invention. The gene or cDNA obtainable from this organism may be cloned and expressed in any *Aspergillus niger* host using known methods.

The following samples were used:

1) "Endo-Pro A", a proline-specific endoprotease was used in experiments with beer. The sample was an ultrafiltration concentrate obtained after ultrafiltration of a fermentation broth obtained after fermentation of an *Aspergillus niger* strain comprising a gene coding for a proline-specific endoprotease. The prolyl-specific activity of the Endo-pro A sample was 5.06 U/ml, determined as described under Methods. The protein concentration was estimated to be 50 g/l, based on the specific activity of a sample of prolyl-specific endoprotease with a purity higher than 90%.

2) "Endo-Pro B", an proline-specific endoprotease was used in experiments with wine. The sample was obtained after purification over a column and had an activity of 6.0 U/ml.

Papain

Collupulin, a liquid papain preparation available from DSM, France was used for experiments with papain. The activity is 5280 NF/mg. One unit NF is the quantity of papain activity that catalyzes the hydrolysis of casein to produce one microgramme equivalent of soluble tyrosine per hour at pH 6.0. The protein concentration in the papain sample was measured, which is 119 g/l (Lowry).

Polyvinylpolypyrrolidone (PVPP)

PVPP used was a commercially available non-water soluble PVPP under the name 'Polyclar AT".

Beer

A malt beer (pilsener type) from "Les Trois Brasseurs" in Lille, France, was used in all experiment performed with beer. The alcohol percentage of this beer was 5.2% (v/v) and the pH was 4.4. This particular beer was chosen because of the relative high amount of turbidity measured in this beer upon chilling, in comparison with other commercially available beers. The beer had a protein concentration of 0.9 g/l, as determined by Lowry's-method.

White Wine

A white wine prepared from white Sauvignon grapes was used without any protein removal treatment. The alcoholic fermentation during wine preparation was performed with a selected yeast VL3 from Lallemand. The oenologic analysis of the wine gave the following results:

| | |
|---|---|
| Sugars (g/l) | 1.1 |
| Ethanol % vol | 12.97 |
| Total Acidity (g $H_2SO_4$/l) | 4.14 |
| Volatil acidity (g $H_2SO_4$/l) | 0.22 |
| PH | 3.46 |
| Free $SO_2$ (mg/l) | 18 |
| Total $SO_2$ (mg/l) | 96 |
| Glycerol (g/l) | 3 |
| Tartric acid (g/l) | 3 |
| Malic acid (g/l) | 2.8 |
| Lactic acid (g/l) | 0.1 |
| Level of Folin | 7 |

Methods

Spectrophotometric Method for Determining the Prolyl-Specific Endoprotease Activity The substrate solution is a 2 mM solution of N-carbobenzoxy-glycine-proline-p-nitro anilide (Z-Gly-Pro-pNA; m.w. 426.43; Bachem) made in a 0.1 M citric acid/0.2 M disodium phosphate buffer pH 5.0 containing 40% dioxan.

To 1 mL of buffer pH 5.0, 250 µl of the substrate solution is added followed by 100 µl of the enzyme solution (larger or smaller volume amounts of enzyme solution should be compensated for by buffer solution). The reaction mixture is incubated at 37° C. and the release of pNA is followed by measuring the absorbance increase at 410 nm.

Activity definition: 1 unit is the enzyme activity that liberates 1 µmol pNA from Z-Gly-Pro-pNA in 1 minute under described reaction conditions. In order to calculate concentrations a molar extinction coefficient (E) of 8,800 M$^{-1}$ is used.

Chill Haze Measurements (Alcohol/Low-Temperature Test According to Lucien Chapon)

Turbidity or haze was measured with a turbidimeter called Tannometer, from Pfeuffer Gmbh, Kitzingen, Germany, in line with the operating instructions from Pfeuffer. Greatly under cooled beer demonstrates a reversible turbidity caused by precipitated polyphenol-protein complexes. The addition of alcohol reduces the solubility of the complexes and thus accelarates the formation of turbidities. To calibrate the Tannometer, a formazine standard solution was prepared as described by Jean de Clerk, "Cours de Brasseries" 2nd Edition, (p. 595-596), Université de Louvain, Belgium. The standard was for turbidity in units EBC. The beer was decarbonated by filtration over a paper filter. Just before performing the Chill haze test ethanol was added to the samples in an amount sufficient to increase the alcohol content to 6% (v/v). The Chill haze test was performed by cooling each sample to −8° C. during 30 min. The haze formed (Turbidity, in units EBC) was quickly measured in the turbidimeter whose measuring chamber was also maintained at −8° C.

Chill haze tests as described for beer may also be performed with worts or alcohol free beers. In those cases ethanol is also added to the samples in an amount sufficient to reach an alcohol content of 10% (v/v) in the samples. The beer haze or turbidity unit used is the ECB which is nephelometric turbidity units as recommended by the European Brewery Convention.

Heating Haze Tests

As described by K. J. Siebert (K. J. Siebert et al, J. Agric. Food Chem. 44 (1996)) haze in beverages like wine or fruit juices can be induced by a heating test. The amount of haze formed is mainly a function of the levels of haze-active proteins and polyphenols in the beverage. In the Heating test, the turbidity of samples (of for example wine or fruit juice) is measured with a turbidimeter before and after heating at 80° C. during 30 min. Before measuring the turbidity, the heated sample is cooled down under cold water until a temperature of 22-25° C. is reached. In the wine trials (see example III) the calibration of the turbidimeter was performed with NTU-formazine standard solutions, for the fruit juice trials (see example V) the NTU turbidity standard solution was purchased from Reagecon, Ireland. NTU=nephelometric turbidity units.

Control Experiments (i) A blank experiment was performed wherein no exogenous protein was added during the incubation.

(ii) An experiment was carried out wherein beer was used that had been treated with a large amount of PVPP (1000 g/hl) before incubation. This experiment allowed the determination of the average amount of haze induced by the chill haze test which is due to polyphenol-protein precipitate, because PVPP removes polyphenols from the beer, and thus interferes with formation of haze.

(iii) Experiments were preformed wherein exogenous proteins (prolyl-specific endoprotease or papain, respectively) were added to beer cooled to 0° C. after incubation at 40° C. for 1 hour. Incubation at 0° C. took place for 15 minutes prior to haze measurements. Since the enzyme and papain are not or hardly active at 0° C., these experiments allowed discrimination between the enzyme activity effect and non-enzymatic protein effects.

Experiments and Comparative Examples Showing the Effect on Haze During Various Tests Example I The Effects of the Addition of a Prolyl-Specific Endoprotease on Haze Formation in Beer To a decarbonated malt beer (Les Trois Brasseurs), protein content: 0.9 g/l. various amounts of a prolyl-specific endoprotease enzyme ("Endo-Pro A", see Materials) were added. Two series of haze-measurements were performed. In the first series, the beer-Endo-Pro A compositions were incubated at 40° C. for 1 hour prior to the Chill haze test. After incubation at 40° C., and just prior to the Chill haze test, ethanol was added to the beer-Endo-Pro A composition in an amount sufficient to increase the alcohol content to 6% (v/v). In the second series, the beer without Endo-Pro A was incubated at 40° C. for 1 hour, and then cooled to 0° C. At 0° C., the Endo-Pro A was added and the resulting compositions were incubated at 0° C. for 15 min. Just prior to the Chill haze test, ethanol was added to the beer-Endo-Pro A composition in an amount sufficient to increase the alcohol content to 6% (v/v).

The amounts of Endo-Pro A added and the percentage of haze reduction relative to the haze measured when no Endo-Pro A was added are shown in Table 1. The amounts of Endo-Pro A added covered a large range from less than 1% of exogenous proteins added to more than 10%, relative to the amount of protein present in the beer.

TABLE 1

Effect of the addition of a prolyl-specific endoprotease enzyme to a beer on the amount of haze after incubation at 40° C. for 1 h

| | "Endo-Pro A" added | | | |
|---|---|---|---|---|
| Trial | µl/10 ml of beer | % of exogenous protein added* | Chill Haze test (EBC | Haze reduction (%) |
| 1 | 0 | 0 | 141 | 0 |
| 2 | 0.45 | 0.25 | 116 | 17.7 |
| 3 | 0.9 | 0.5 | 101 | 28.4 |
| 4 | 1.8 | 1 | 87.4 | 38.0 |
| 5 | 3.6 | 2 | 81.1 | 42.5 |
| 6 | 5.4 | 3 | 69.0 | 51.1 |
| 7 | 9 | 5 | 61.3 | 56.5 |
| 8 | 18 | 10 | 48.5 | 65.6 |
| 9 | 36 | 20 | 39.9 | 71.7 |
| 10 | 54 | 30 | 33.4 | 76.3 |

*"% of exogenous enzyme added" reflects the amount of Endo-Pro A"-enzyme added expressed as a percentage of the total amount of proteins present in the beer before addition of the enzyme.

TABLE 2

Effect of prolyl-specific endoprotease enzyme to a beer on the amount of haze after incubation at 0° C. for 15 min

| | Endo-Pro added | | | |
|---|---|---|---|---|
| Trial | µl/10 ml of beer | % of exogenous protein added | Chill Haze test (EBC | Haze reduction (%) |
| 1 | 0 | 0 | 141 | 0 |
| 2 | 0.45 | 0.25 | 141 | 0 |
| 3 | 0.9 | 0.5 | 141 | 0 |
| 4 | 1.8 | 1 | 143 | −1.4 |
| 5 | 3.6 | 2 | 145 | −2.8 |
| 6 | 5.4 | 3 | 138 | 2.1 |

TABLE 2-continued

Effect of prolyl-specific endoprotease enzyme to a beer on the amount of haze after incubation at 0° C. for 15 min Endo-Pro added

| Trial | μl/10 ml of beer | % of exogeneous protein added | Chill Haze test (EBC | Haze reduction (%) |
|---|---|---|---|---|
| 7 | 9 | 5 | 138 | 2.1 |
| 8 | 18 | 10 | 130 | 7.8 |
| 9 | 36 | 20 | 126 | 10.6 |
| 10 | 54 | 30 | 120 | 14.9 |

Table 1 clearly illustrates that less haze is formed upon chilling when a prolyl-specific endoprotease is added to beer at a temperature when the protease is active prior to chilling. Table 2 clearly illustrates that there is some effect when a prolyl-specific endoprotease is added to the beer at a temperature so low that the protease is not or hardly active, but the effect is very small in comparison to the effect observed when the protease is added at a temperature where it is active.

Comparative Experiment A

The Effects of the Addition of Papain on Haze Formation in Beer

To a decarbonated malt beer (Les Trois Brasseur), protein content: 0.9 g/l, various amounts of papain (from 0 to 100 g/hl) were added. Two series of chill haze-measurements were performed. For the first series, the beer-papain compositions were incubated at 40° C. for 1 hour prior to the Chill haze test. Ethanol was added to the incubated samples to reach 6% alcohol (v/v/) prior to the haze measurements. In the second series, beer samples were incubated at 40° C. for 1 hour and subsequently cooled to 0° C. Then, papain was added and the samples were incubated at 0° C. for 15 min. The amounts of papain added and the percentage of haze reduction relative to the haze measured when no papain was added are shown in Table 3.

TABLE 3

Effect of papain on the amount of haze formed in beer after incubation at 40° C. for 1 h Papain added

| Trial | g/hl beer | % of exogeneous protein added | Chill Haze test (EBC) | Haze reduction (%) |
|---|---|---|---|---|
| 1 | 0 | 0 | 143 | 0 |
| 2 | 0.2 | 0.03 | 140 | 2.1 |
| 3 | 0.5 | 0.07 | 133 | 7.0 |
| 4 | 1 | 0.13 | 119 | 16.8 |
| 5 | 2 | 0.26 | 94.1 | 34.2 |
| 6 | 3[(1)] | 0.40 | 91.6 | 35.9 |
| 7 | 5 | 0.66 | 83.8 | 41.4 |
| 8 | 8 | 1.06 | 82.4 | 42.4 |
| 9 | 10 | 1.32 | 84.0 | 41.3 |
| 10 | 100 | 13.22 | 81.6 | 42.9 |

[(1)] 3 g/hl is the maximal dosage recommended

TABLE 4

Effect of papain on the amount of haze after incubation at 0° C. for 15 min

Papain added

| Trial | g/hl beer | % of exogeneous protein added | Chill Haze test (EBC)C | Haze reduction (%) |
|---|---|---|---|---|
| 1 | 0 | 0 | 143 | 0 |
| 2 | 0.2 | 0.03 | 139 | 2.8 |
| 3 | 0.5 | 0.07 | 136 | 4.9 |
| 4 | 1 | 0.13 | 135 | 5.6 |
| 5 | 2 | 0.26 | 134 | 6.3 |
| 6 | 3 | 0.40 | 132 | 7.7 |
| 7 | 5 | 0.66 | 136 | 4.9 |
| 8 | 8 | 1.06 | 130 | 9.1 |
| 9 | 10 | 1.32 | 122 | 14.7 |
| 10 | 100 | 13.22 | 138 | 3.5 |

The results in Table 3 illustrate the effect of papain on the amount of haze formed in beer upon chilling. It is clear that the effect of papain on haze levels off when papain is added in an amount of 3 g/hl and higher. Apparently, it is not possible to achieve the same amount of haze reduction with papain as with a prolyl-specific endoprotease.

Comparative Experiment B

The Effects of the Addition of PVPP on Haze Formation in Beer

In both beer-prolyl-specific endoprotease experiments and the beer-papain experiments, a control experiment was done by adding a large amount of PVPP (1000 g/hl) to the beer prior to incubation. After 15 min of mixing the PVPP was removed by filtration (No prolyl-specific endoprotease enzym or papain was added). In both controls almost no haze were formed during the chill haze test. Since it is known that PVPP removes polyphenols from beverages, these control experiments indicate that polyphenols do take part in haze formation in beer. To measure the PVPP effect on beer haze stability, different amounts of PVPP were added to a decarbonated beer and removed by filtration after 15 min of mixing. Prior to adding the PVPP the beer was incubated during 1 h at 40° C.

Table 5 shows the effect of the addition of various amounts of PVPP on the amount of haze present in beer upon chilling. No Endo-Pro A or papain was added.

TABLE 5

Effect of PVPP on the amount of haze present in beer upon chilling

| PVPP added (g/hl) | Chill Haze test (EBC) | Haze reduction (%) |
|---|---|---|
| 0 | 133 | 0 |
| 10 | 131 | 1.5 |
| 20 | 115 | 13.5 |
| 30[(1)] | 103 | 22.6 |
| 50 | 65.2 | 51.0 |
| 80 | 48.4 | 63.6 |
| 100 | 42.1 | 68.3 |
| 500 | 17.2 | 87.1 |
| 1000 | 9.5 | 92.9 |

[(1)] 30 g/hl maximal dosage used in breweries

In Table 3 it is shown that the addition of 3 g of Papain/hl of beer (which is the maximal dosage recommended in the beer industry) after incubation at 40° C. for 1 hour induces an haze decrease of almost 36%. In the case of addition of the prolyl-specific endoprotease, the addition of 1%. (relative to the amount of protein in the beer) of prolyl-specific endoprotease after incubation at 40° C. for 1 hour induces a decrease of a beer chill haze of 38% (see Table 1). In breweries, PVPP is generally added in a quantity that does not exceed 30 g/hl. Since PVPP reduces haze by around 20% when it is added in that quantity, it can be concluded that both papain and prolyl-specific endoprotease enzymes are better haze inhibitors than PVPP.

Example II

Endo-Pro Addition on a 100% Malt Mash and Haze Reduction in a 100% Malt Wort

The objective was to determine if the addition of prolyl-specific endoprotease to a 100% malt mash could result in an haze reduction in the final malt wort.

Each mashing trial begins with the mixing of 25 g of milled malt with 100 ml of water. Then, the mash is heated to 50° C. and after the addition of an amount of "Endo-Pro A" the mash is treated according to a step-wise heating procedure to four successively higher temperatures. Table 6 shows that mashing temperature profile. During all the mashing the mash was stirred at 200 rpm. At the end of the mashing, the mash is kept at room temperature and water was added to compensate the water evaporation. Then, the mash was filtered on paper to separate the wort (liquid) from the solids.

TABLE 6

Mashing temperature profile

| Steps | Temperature | time |
| --- | --- | --- |
| 1 | 50° C. | 30 min |
| temperature increase | 1° C./min | 13 min |
| 2 | 63° C. | 30 min |
| temperature increase | 1° C./min | 10 min |
| 3 | 72° C. | 30 min |
| temperature increase | 1° C./min | 4 min |
| 4 | 77° C. | 10 min |

0, 200 & 500 µl Endo-Pro A was added to the mashes, respectively. A control experiment was performed wherein 500 µl of Endo-Pro A was used that was deactivated by heating it to 90° C. during 15 min. The turbidity or haze of the wort was measured at room temperature and after a chill haze test. Wort chill tests are performed as described in the Alcohol/low-temperature test according to Chapon (Chill Haze test—Pfeuffer Operating instructions) adding ethanol to reach 10% (v/v) in the sample as recommended by Chapon for alcohol-free beers.

TABLE 7 effect of the addition of prolyl-specific endoprotease to 100% malt mashes on the amount of haze formed in the resulting 100% malt worts (after Chill haze test)

| Trial | Endo-Pro A added in the mash (µl) | Wort initial turbidity (EBC[1]) | Wort turbidity after Chill Haze test (EBC) | Haze induced by the Chill Haze test (ΔEBC) | Endo-Pro A haze reduction effect (%) |
| --- | --- | --- | --- | --- | --- |
| 1 | 0 | 10 | 158.5 | 148.5 | 0 |
| 2 | 200 | 15.9 | 59.2 | 43.3 | 70.8 |
| 3 | 500 | 22.5 | 49.1 | 26.6 | 82.1 |
| 4 | 500 (desactivated) | 12.1 | 160.5 | 148.4 | 0.1 |

(1) EBC: nephelometric turbidity units recommended by the European Brewery Convention The results in Table 7 clearly indicate that when a prolyl-specific endoprotease has been added to a malt mash, the resulting wort is much less turbid upon cooling than a wort prepared without the addition of a prolyl-specific endoprotease.

To study the Endo-Pro A effect, a chill haze test was performed on malt wort. It was observed that the addition of a prolyl-specific endoprotease decreased the wort chill haze. A decrease in haze formed in the Chill haze test was observed even at low quantities of prolyl-specific endoprotease enzyme added. When the enzyme is deactivated prior to be added in the mash, the stabilization effect disappears completely i.e. the amount of haze formed is no longer reduced. The haze decrease induced by the addition of a prolyl-specific enzyme is very important. In the example a haze reduction of up to 82% was achieved.

In order to compare the effects of the addition of a prolyl-specific endoprotease enzyme in malt worts and in barley worts, experiments were performed wherein different amounts of Endo-Pro A were added in barley mashes. The pH were respectively 5.6 in malt worts and 6.1 in barley worts. The results obtained with barley worts chill haze tests showed that as observed previously for malt worts, the treatment of barley mashes by a prolyl-specific endoprotease induces an important reduction of barley worts chill haze. Both malt and barley mashes treated with a prolyl-specific endoprotease result in highly stabilized worts but the effect is stronger in malt worts than in barley worts. Indeed, the addition in the mash of 200 µl of Endo-Pro A induced a haze reduction of around 59% in barley worts and more than 70% in malt worts. The trials performed with 500 µl of Endo-Pro A increased the haze reduction until 82% in malt worts and did not improve the haze reduction in barley worts compared to the 200 µl Endo-Pro A experiment. Surprisingly, the addition of Endo-Pro A to barley mashes resulted in clear filtered worts while the non-Endo-Pro treated mashes resulted in cloudy filtered worts (the barley mash filtrations were performed at room temperature and the turbidity of the worts was measured at room temperature without ethanol addition). That effect is observed whatever the amount of prolyl-specific endoprotease added in the barley mashes.

Example III

Haze Reduction in Wine

Different dosages (0, 30, 60 150 µl) of a prolyl-specific endoprotease (Endo-Pro B) having a specific activity of 6.0 U/ml were added to flasks containing 500 ml of white wine (wine as described under "Materials") and incubated at room temperature (22-25° C.) for 19 days under a nitrogen atmosphere. The wine haze stability was measured after 0, 6, 8, 12 and 19 days using the Heating test as described under "Methods".

The results of the experiments are shown in Table 8. In Table 8, wine turbidity or haze is expressed in nephelos turbidity units (NTU). ΔNTU=turbidity in NTU measured on wine samples after heating—turbidity in NTU measured on wine samples before heating. The quantity of bentonite required to stabilize the proteins of the wine was calculated according to the formula: (1.48×Δ NTU)+2. As is known, less bentonite is needed to prevent haze formation in wine when a wine is less susceptible to haze formation.

TABLE 8

Effect of the addition of a prolyl-specific endoprotease enzyme to a white wine the amount of haze formed after heating the wine

| Incubation time | Endo-Pro added (μl/500 ml) | Turbidity before heating (NTU) | Turbidity after heating (NTU) | Δ NTU | quantity of bentonite required (g/hl) | haze reduction (%) | Decrease of the quantity of bentonite required (%) |
|---|---|---|---|---|---|---|---|
| 0 | 0 μl (Control) | 36.8 | 74.5 | 38 | 58 | | |
| 6 days | 0 μl (Control) | 25.8 | 63.8 | 38 | 58 | 0 | 0 |
| | 30 μl | 20.2 | 53.5 | 33 | 51 | 13 | 12 |
| | 60 μl | 21.6 | 56 | 34 | 53 | 11 | 9 |
| | 150 μl | 20.5 | 43.3 | 23 | 37 | 39 | 36 |
| 8 days | 0 μl (Control) | 26.4 | 68 | 42 | 64 | 0 | 0 |
| | 30 μl | 31.4 | 60.2 | 29 | 45 | 31 | 30 |
| | 60 μl | 29.6 | 56.2 | 27 | 41 | 36 | 36 |
| | 150 μl | 25.1 | 48.4 | 23 | 36 | 45 | 44 |
| 12 days | 0 μl (Control) | 24.4 | 50.1 | 26 | 40 | 0 | 0 |
| | 30 μl | 23 | 36.9 | 14 | 23 | 46 | 43 |
| | 60 μl | 23 | 36.6 | 14 | 23 | 46 | 43 |
| | 150 μl | 23.9 | 37.9 | 14 | 23 | 46 | 43 |
| 19 days | 0 μl (Control) | 6.5 | 23.2 | 17 | 26 | 0 | 0 |
| | 30 μl | 5.8 | 11.2 | 5 | 10 | 71 | 62 |
| | 60 μl | 7 | 11.1 | 4 | 8 | 76 | 69 |
| | 150 μl | 8.5 | 13.7 | 5 | 10 | 71 | 62 |

The results in Table 8 show that the addition of a prolyl-specific endoprotease to a white wine before heating reduces the haze formed in the wine after heating. After 6 days of incubation at room temperature the effect is observed. Indeed, the haze decrease reaches 39% with 150 μl of the Endo-Pro B-added and around 12% with 30 μl or 60 μl of Endo-Pro B. After 12 days and whatever the amount of the prolyl-specific endoprotease used the haze reduction reaches 46% and exceeds 70% after 19 days. Therefore, it is clear that a prolyl-specific endoprotease can be used to avoid or to strongly reduce the quantity of bentonite required to stabilize wine against haze formation.

Example IV

Haze Reduction in Strawberry Juice

A strawberry fruit juice was prepared as follows: strawberries were defrosted and crushed, and subsequently blanched (heated) at 90° C. in order to destroy all endogenous enzymes such as polyphenol oxidases, and to denaturate proteins. The crushed strawberries were then cooled to 50° C., macerated for 30 min at 50° C. with 600 g/t or Rapidase BE super (a commercial enzyme product of DSM, France) and pressed in a pneumatic press. In order to remove the denatured proteins the resulting mixture was centrifuged at a speed of 8000 rpm and filtered. The strawberry-juice was collected. An acidified alcohol test was negative, which confirmed that the juice was pectin free. The pH value of the juice was 3.3.

Endo-Pro A/strawberry juice incubations: Different volumes (0, 5, 10, 20 μl) of Endo-Pro A (5.06 U/ml) were added to 100 ml of strawberry juice and incubated at 50° C. for 60 min. Two control experiments were performed, (i) one by adding 20 μl of deactivated Endo-Pro A (incubated 30 min at 80° C.) and (ii) a second control by adding 200 mg of PVPP to 20 ml of strawberry juice previously incubated 1 h at 50° C. After having been mixed for 15 min at room temperature the PVPP was removed by centrifugation.

Juice Heating test: the juice turbidity was measured before and after heating the fruit juice samples at 80° C. during 30 minutes. Before measuring the turbidity, the heated juices were cooled down under cold water.

The turbidity measurements were performed in a turbidimeter previously calibrated with NTU turbidity standards from Reagecon (Ireland)

TABLE 9

Effect of the addition of prolyl-specific endoprotease on the haze in strawberry juice

| Trial | Endo-Pro A added (μl/100 ml) | Turbidity before heating (NTU) | Turbidity after heating (NTU) | ΔNTU | reduction effect (%) |
|---|---|---|---|---|---|
| 1 | 0 | 10.1 | 17.5 | 7.4 | 0 |
| 2 | 5 | 9.5 | 15.0 | 5.5 | 25.7 |
| 3 | 10 | 9.4 | 15.4 | 6.0 | 18.9 |

TABLE 9-continued

Effect of the addition of prolyl-specific endoprotease on the haze in strawberry juice

| Trial | Endo-Pro A added (μl/100 ml) | Turbidity before heating (NTU) | Turbidity after heating (NTU) | ΔNTU | reduction effect (%) |
|---|---|---|---|---|---|
| 5 | 10 (deactivated) | 10.2 | 16.9 | 6.7 | 9.4 |
| 6 | PVPP | 1.4 | 2.3 | 0.9 | |

The results in Table 9 show that the addition of 5 μl of Endo pro A in 100 ml strawberry juice decreased haze formed after a juice heating test by 25.7%. The addition of 10 μl of Endo-Pro A to 100 ml strawberry juice did not improve the haze reduction effect compared to the 5 μl trial. Possibly, the enzyme action is maximal with 5 μl and with more enzyme addition more protein precipitation is obtained.

Deactivated enzyme still reduced the amount of haze formed, however, the effect was much less pronounced. After the addition of PVPP, hardly any haze was observed, but the color of the sample was also removed. The fact that the addition of PVPP results prevents haze formation indicates that also in strawberry juice haze is probably the result of polyphenol-protein interactions.

The invention claimed is:

1. A proteolytic method to reduce haze in a beverage, which method comprises adding a proline-specific endoprotease protein-containing preparation to the beverage, wherein the proline-specific endoprotease cuts a protein or peptide at places where the protein or peptide contains a prolyl residue to proteolytically reduce haze in the beverage, wherein at least 70% of the proteins in the preparation are said proline-specific endoprotease, the proline-specific endoprotease being comprised of an amino acid sequence which has at least 95% sequence identity with the amino acid sequence of SEQ ID NO: 5.

2. The method of claim 1, wherein said endoprotease has maximum prolyl-specific activity at a pH corresponding to the pH of the beverage to which it is added.

3. The method of claim 1, wherein the beverage contains at least one protein.

4. The method of claim 3, wherein the beverage contains polyphenols.

5. The method of claim 1, wherein the beverage has a pH value below 7.

6. The method of claim 3, wherein at least 150 milli-units of proline-specific endoprotease activity, which can be determined using Z-Gly-Pro-pNA as substrate, is added to the beverage per gram protein in the beverage.

7. The method of claim 6, wherein at least 500 milli-units of proline-specific endoprotease activity, which can be determined using Z-Gly-Pro-pNA as substrate, is added to the beverage per gram protein in the beverage.

8. The method of claim 7, wherein at least 1 unit of proline-specific endoprotease activity, which can be determined using Z-Gly-Pro-pNA as substrate, is added to the beverage per gram protein in the beverage.

9. The method of claim 1, wherein the beverage is beer.

10. The method of claim 1, wherein the beverage is wine.

11. The method of claim 1, wherein the beverage is fruit juice.

12. The method of claim 9, wherein the proline-specific endoprotease protein containing preparation is added to a mash.

13. The method of claim 9, wherein the proline-specific endoprotease protein containing preparation is added to a beer before haze is formed.

14. The method of claim 9, wherein the proline-specific endoprotease protein containing preparation is added to a fermented beer after haze has been formed.

15. The method of claim 10, wherein the proline-specific endoprotease protein containing preparation is added to a fermented wine.

16. The method of claim 1, wherein the proline-specific endoprotease is isolated or purified prior to addition to the beverage.

17. A method to reduce haze in a beverage, which method comprises adding a proline-specific endoprotease to the beverage to reduce haze therein, wherein the proline-specific endoprotease cuts a protein or peptide at places where the protein or peptide contains a prolyl residue, wherein the proline-specific endoprotease is comprised of an amino acid sequence which has at least 95% sequence identity with the amino acid sequence of SEQ ID NO: 5, wherein the proline-specific endoprotease is produced by recombinant expression, and wherein the proline-specific endoprotease is added as a filtrate obtained from a fermentation broth of cells which are modified to contain a recombinant nucleic acid construct for production of the proline-specific endoprotease, and wherein said filtrate contains proteins and at least 70% of the proteins in the filtrate are said proline-specific endoprotease.

18. A method to reduce haze in a beverage, which method comprises adding a proline-specific endoprotease to the beverage to reduce haze therein, wherein the proline-specific endoprotease is encoded by a polynucleotide which hybridizes under high stringency conditions of 0.3M sodium chloride, 0.03M sodium citrate, and 60° C. with the complement of the nucleotide sequence of SEQ ID NO: 1, and wherein the proline-specific endoprotease is produced by recombinant expression said proline-specific endoprotease being added to the beverage in a protein containing preparation wherein at least 70% of the proteins in the preparation are said proline-specific endoprotease.

19. A proteolytic method to reduce haze in a beverage, which method comprises adding a proline-specific endoprotease protein-containing preparation to the beverage to proteolytically reduce haze therein, wherein at least 70% of the proteins in the preparation are said proline-specific endoproteinase, the proline-specific endoprotease being comprised of the amino acid sequence of SEQ ID NO: 5.

20. The method of claim 18, wherein the proline-specific endoprotease is encoded by a polynucleotide comprised of the nucleotide sequence of SEQ ID NO: 1.

21. The method of claim 18, wherein the beverage contains at least one protein.

22. The method of claim 21, wherein the beverage contains polyphenols.

23. The method of claim 18, wherein the beverage has a pH value below 7.

24. The method of claim 21, wherein at least 150 milli-units of proline-specific endoprotease activity, which can be determined using Z-Gly-Pro-pNA as substrate, is added to the beverage per gram protein in the beverage.

25. The method of claim 24, wherein at least 500 milli-units of proline-specific endoprotease activity, which can be determined using Z-Gly-Pro-pNA as substrate, is added to the beverage per gram protein in the beverage.

26. The method of claim 25, wherein at least 1 unit of proline-specific endoprotease activity, which can be determined using Z-Gly-Pro-pNA as substrate, is added to the beverage per gram protein in the beverage.

27. The method of claim 18, wherein the beverage is beer.

28. The method of claim 18, wherein the beverage is wine.

29. The method of claim 18, wherein the beverage is fruit juice.

30. The method of claim 27, wherein the proline-specific endoprotease protein containing preparation is added to a mash.

31. The method of claim 27, wherein the proline-specific endoprotease protein containing preparation is added to a beer before haze is formed.

32. The method of claim 27, wherein the proline-specific endoprotease protein containing preparation is added to a fermented beer after haze has been formed.

33. The method of claim 28, wherein the proline-specific endoprotease protein containing preparation is added to a fermented wine.

34. The method of claim 18, wherein the proline-specific endoprotease is isolated or purified prior to addition to the beverage.

35. A method to reduce haze in a beverage, which method comprises adding a proline-specific endoprotease to the beverage to reduce haze therein, wherein the proline-specific endoprotease is comprised of the amino acid sequence of SEQ ID NO: 5, wherein the proline-specific endoprotease is produced by recombinant expression, and wherein the proline-specific endoprotease is added as a filtrate obtained from a fermentation broth of cells which are modified to contain a recombinant nucleic acid construct for production of the proline-specific endoprotease, and wherein said filtrate contains proteins and at least 70% of the proteins in the filtrate are said proline-specific endoprotease.

* * * * *